(12) United States Patent
Lagard et al.

(10) Patent No.: US 7,531,365 B2
(45) Date of Patent: May 12, 2009

(54) ANALYSIS OF THE HEADSPACE PROXIMATE A SUBSTRATE SURFACE CONTAINING FRAGRANCE-CONTAINING MICROCAPSULES

(75) Inventors: Danielle Lagard, Lodi, NJ (US); George Allen Reiner, Middletown, NJ (US); Gary William Christensen, Neptune, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 996 days.

(21) Appl. No.: 10/753,847

(22) Filed: Jan. 8, 2004

(65) Prior Publication Data

US 2005/0153455 A1 Jul. 14, 2005

(51) Int. Cl.
*G01N 1/22* (2006.01)
*G01N 7/00* (2006.01)
*D06M 23/06* (2006.01)
*C11D 3/50* (2006.01)

(52) U.S. Cl. .................... 436/181; 436/148; 73/864.84; 252/8.91; 512/4

(58) Field of Classification Search ................. 436/181, 436/148; 73/864.84; 252/8.91; 512/4
See application file for complete search history.

(56) References Cited

U.S. PATENT DOCUMENTS

| 2,800,458 | A | 7/1957 | Green |
| 3,400,100 | A | 9/1968 | Van Dort et al. |
| 3,516,846 | A | 6/1970 | Matson |
| 3,644,227 | A | 2/1972 | Factor |
| 3,703,564 | A | 11/1972 | White |
| 3,839,220 | A | * 10/1974 | Barchas ......................... 516/7 |
| 4,016,098 | A | * 4/1977 | Saeki et al. ................... 264/4.3 |

(Continued)

FOREIGN PATENT DOCUMENTS

GB    2006709    9/1978

(Continued)

OTHER PUBLICATIONS

De, et al, Brimonidine formulation in polyacrylic acid nanoparticles for ophthalmic delivery, J.Microencapsulation, 2003, vol. 20, No. 3, 361-374.

(Continued)

*Primary Examiner*—Jill Warden
*Assistant Examiner*—Lore Ramillano
(74) *Attorney, Agent, or Firm*—Elizabeth M. Quirk; XuFan Tseng; Joseph F. Leightner

(57) ABSTRACT

Described is apparatus and a process for the enablement of functional product analysis of the headspace proximate one or more substrate, such as hair, fabric or skin, surfaces having affixed thereto functional product, a fragrance composition and/or malodor counteractant composition-containing microcapsules. The apparatus employs mobile microcapsule-abrading solid objects, including agitating stainless steel spheres during analyte collection in a gas-flow/trapping tube analyte collection apparatus. The reciprocating motion and the air-flow are commenced simultaneously thereby enabling the solid objects to become mobile and to effectively abrade the microcapsules affixed to the semi-solid surfaces. The volatile substance contained in the microcapsules is then emitted from the resulting ruptured microcapsules into the headspace above them, and the air flow carries the volatile substance molecules into the trapping means, which is then subjected to extraction followed by analysis of the extract, such as gas chromatography, mass spectral analysis, infra-red analysis and NMR analysis.

22 Claims, 9 Drawing Sheets

U.S. PATENT DOCUMENTS

| | | |
|---|---|---|
| 4,087,376 A | 5/1978 | Foris et al. |
| 4,100,103 A | 7/1978 | Foris et al. |
| 4,157,983 A | 6/1979 | Golden |
| 4,173,418 A | 11/1979 | Vork |
| 4,406,816 A | 9/1983 | Sliwka |
| 4,431,779 A | 2/1984 | White et al. |
| 4,493,869 A | 1/1985 | Sweeny et al. |
| 4,801,645 A | 1/1989 | Nishio et al. |
| 4,819,835 A | 4/1989 | Tasaki |
| 4,832,978 A | 5/1989 | Lesser |
| 4,973,422 A * | 11/1990 | Schmidt ............... 510/337 |
| 5,237,035 A | 8/1993 | O'Lenick, Jr. et al. |
| 5,324,649 A | 6/1994 | Arnold et al. |
| 5,672,456 A | 9/1997 | Chamberlain et al. |
| 5,879,920 A | 3/1999 | Dale et al. |
| 5,971,599 A | 10/1999 | Bothers |
| 6,042,792 A | 3/2000 | Shefer et al. |
| 6,248,364 B1 | 6/2001 | Sengupta et al. |
| 6,261,483 B1 | 7/2001 | Frank et al. |
| 6,444,326 B1 | 9/2002 | Smith |
| 6,495,375 B2 | 12/2002 | Ledig |
| 6,511,760 B1 | 1/2003 | Barone et al. |
| 6,511,852 B1 | 1/2003 | Ledig |
| 6,545,084 B2 | 4/2003 | Brown et al. |
| 6,579,002 B1 | 6/2003 | Bartick et al. |
| 2001/0008874 A1 | 7/2001 | Igari et al. |
| 2001/0016259 A1 | 8/2001 | Campbell et al. |
| 2001/0030906 A1 | 10/2001 | Friedman |
| 2001/0056177 A1 | 12/2001 | Becker et al. |
| 2002/0098761 A1 | 7/2002 | Nishimoto et al. |
| 2002/0099121 A1 | 7/2002 | Oshima et al. |
| 2002/0193275 A1 | 12/2002 | Christensen, Jr. |
| 2003/0069482 A1 | 4/2003 | Workman, Jr. et al. |
| 2003/0081499 A1 | 5/2003 | Friedman |
| 2003/0125222 A1 | 7/2003 | Jahns et al. |
| 2003/0176282 A1 | 9/2003 | Seehafer et al. |
| 2003/0185960 A1 | 10/2003 | Augustin et al. |
| 2003/0194416 A1 | 10/2003 | Shefer et al. |
| 2004/0072720 A1 * | 4/2004 | Brain et al. ............... 512/4 |

FOREIGN PATENT DOCUMENTS

| | | |
|---|---|---|
| GB | 2073132 | 3/1981 |
| GB | 2062570 | 5/1981 |
| WO | WO 98/28396 | 7/1998 |

OTHER PUBLICATIONS

Lee, et al, Microencapsulation of fragrant oil via in situ polymerization:effects of pH and melamine-formaldehyde molar ratio, J.Microencapsulation, 2002, vol. 19, No. 5, 559-569.

Elmore, et al, Comparison of Dynamic Headspace Concentration on Tenax with Solid Phase Microextraction for the Analysis of Aroma Volatiles, J.Agric.Food Chem., 1997, 45, 2638-2641.

Becker, et al, Genencor International Inc., Palo Alto, California, Chapter 15, Formulation of Detergent Enzymes, 299-325.

* cited by examiner

ANALYSIS OF THE HEADSPACE PROXIMATE A SUBSTRATE SURFACE CONTAINING FRAGRANCE-CONTAINING MICROCAPSULES

FIELD OF THE INVENTION

Apparatus and processes for conducting headspace analysis of microencapsulated fragrance compositions employing mobile microcapsule-abrading solid objects during analysis and collection of the fragrance composition is disclosed.

BACKGROUND OF THE INVENTION

The scientific designing of systems for effecting controlled and sustained release of fragrances and malodour counteractants from semi-solid substrates including fabric, human skin and hair surfaces into the environment proximate such substrates has been the subject of ongoing investigations. Such systems include the targeted deposition onto substrate surfaces for extended periods of time of rupturable microcapsules composed of thin polymeric walls and containing substantial quantities of monophasic liquid compositions of such fragrance compositions and malodour counteractant compositions.

In designing and then employing such systems it has been found necessary to achieve optimization of (a) the nature and content of the targeted microcapsules, such as microcapsule dimensions, including average effective diameters and average wall thickness, polymer wall composition, specific ingredients, weight ratio of capsule wall: functional product composition, ratios of microcapsule volume:substrate area to which microcapsules are adhered and loaded, microcapsule weight:substrate area to which microcapsules are adhered in combination with (b) their respective rates of release of the functional products contained therein as a function of time, temperature and abrading use thereof, such as rubbing fabrics or skin having the microcapsules adhered thereto or, brushing of groups of hair follicles to which the microcapsules are adhered to.

Accordingly, a need has been found to exist for (a) simulating such abrading use in the laboratory, and (b) enabling analytical measurement of the results of such abrading use on a continuing basis, including analytical measurement over an extended period of time of the several components of the headspace composition proximate the microcapsule-bearing substrate being abraded, as well as the rate of change of the several components of the headspace composition proximate the microcapsule-bearing substrate being abraded with respect to time and temperature.

The prior art discloses techniques for enabling the analysis of fragrances, including movement-activated fragrances adsorbed onto a porous substrate and evolving into the environment proximate such substrate, such as, towels as disclosed in U.S. Pat. Nos. 6,511,852 and 6,495,375. In addition, the use of relatively large and dense objects having a high degree of surface hardness, such as, steel spheres, for causing formation of dust from vinyl polymer-coated granules for the purpose of enabling analytical measurements, such as, analysis of vinyl polymer-coated enzyme granule dust is disclosed in U.S. Pat. Nos. 5,324,649 and 5,879,920 and published U.S. Patent Applications 2001/0056177 and 2002/0193275, wherein reference is made therein to the "Heubach attrition test". The Heubach attrition test is described in detail in "Enzymes in Detergency", ed. Jan H. Van Ee et al. (Marcel Dekker, N.Y., 1997) at pages 310-312 of Chapter 15 (Becker et al. "Formulation of Detergent Enzymes"). A schematic diagram of the Heubach apparatus is set forth on page 312, FIG. 3b. In addition, (i) for effecting particle size reduction, U.S. Patent Application 2001/0016259 A1, discloses the use of mobile steel balls maintained in motion by means of the operation of a shaker, and (ii) for effecting solubilization of solids in liquids, U.S. Pat. No. 5,672,456 discloses the use of a reciprocating shaker to hasten the dissolution process.

However, nothing in the prior art discloses or infers any method or apparatus for effectively and efficiently enabling the qualitative and/or quantitative chemical analysis of the components of the headspace above abraded microencapsulates containing fragrances and/or malodour counteractants as a result of the simulated abrading use such as rubbing and/or brushing on such functional product-containing microcapsules which are affixed to a semi-solid substrate, including fabric, skin or hair follicles.

SUMMARY OF THE INVENTION

Our invention is directed to apparatus and a process for the enablement of functional product, such as fragrance and/or malodour counteractant materials; quantitative and qualitative analysis of the headspace proximate one or more semi-solid substrate, having affixed thereto functional product, containing microcapsules immediately subsequent to the abrading of the microcapsules, such as, rubbing and/or brushing the substrate to which the microcapsules are adhered. The apparatus employs mobile microcapsule-abrading solid objects, such as, agitating stainless steel balls during analyte collection in a gas-flow/trapping tube analyte collection apparatus, the entirety of which is subjected to reciprocating motion on a horizontal plane. Initially, prior to operation of the apparatus of our invention, the microcapsule-abrading objects are interleaved between microcapsule-bearing semi-solid surface sections contained in the hollow enclosure part of the apparatus. The reciprocating motion and the air-flow are commenced simultaneously thereby enabling the solid objects to become mobile and to effectively abrade the microcapsules affixed to the semi-solid surfaces thereby simulating the rubbing or brushing which takes place during actual use of the microcapsule-bearing substrate. The contained volatile substance is then emitted from the resulting ruptured microcapsules into the headspace above them, and the air flow carries the volatile substance molecule into the trapping means which includes a trapping substance, such as, TENAX, BUCHEM, B.V. of Apeldoorn, Netherlands, which entraps molecules of each component of the volatile substance. The trapping substance containing the entrapped volatile substance is then removed from the apparatus and the volatile substance is extracted therefrom and analyzed using such techniques as gas chromatography, nuclear magnetic resonance analysis and mass spectral analysis.

More specifically, our invention is directed to apparatus for quantitatively and qualitatively enabling the analysis of a volatile functional substance, such as, a fragrance composition and/or a malodour counteractant composition encapsulated in a plurality of rupturable microcapsules each of which (a) has a rupturable polymeric wall; (b) has an outside diameter in the range of from about 0.01 microns to about 1000 microns and has a wall thickness in the range of from about 0.01 microns to about 100 microns; (c) contains from about 50% to about 97% by weight of volatile substance or solution of volatile substance; and (d) is releasably adhered to the surface of a semi-solid substrate section, comprising:

(i) a horizontally-situated reciprocatingly-movable horizontal substantially solid substantially planar surface located in the 'X-Y' plane associated with a driving means therefor for effecting a reciprocating motion of said substantially solid substantially planar surface at a controllable frequency, $\phi$ or set of frequencies, $\phi_1$, $\phi_2$, $\phi_3$, $\phi_n$ (wherein n is an integer in the range of from 1 to about 20) for a determined period of time, $\theta$;

(ii) substantially removably supported on said substantially solid substantially planar surface, a hollow enclosure means having a void space surrounded by a gas-impermeable horizontally-disposed base, a gas-impermeable horizontally-disposed lid and a gas-impermeable substantially cylindrical wall extending upwardly from and circumventing said base and extending downwardly from and circumventing said lid, said lid and/or said cylindrical wall having at least one exit port means and an entry port means therethrough, said hollow enclosure means being maintained in a stable, rigid, upright configuration during operation of said apparatus and being adapted to stably contain (I) a plurality of mobile solid-state spheres and/or ellipsoids each of which has a weight of from about 1 gm to about 100 gm, a density of from about 2 gm/cc to about 10 gm/cc, an average diameter of from about 0.5 cm to about 3.0 cm., a high tensile strength, e.g., in the range of from about 60,000 psi (pounds per square inch) to about 300,000 psi, and a surface hardness Knoop value of from about 160 to about 220 or a Mohs hardness value in the range of from about 4 to about 8.5 or a Brinell hardness value of from about 110 to about 750 and (II) inter-leaved between layers of said plurality of spheres and/or ellipsoids, semi-solid substrate sections having laminar surfaces, each of which has adhered thereto a plurality of said volatile substance-containing rupturable microcapsules each of which has a surface hardness Knoop value of from about 10 to about 20 or a Mohs hardness value in the range of from about 0.5 to about 2.0 or a Brinell hardness value in the range of from about 2 to about 15 and a microcapsule wall tensile strength several orders of magnitude less than the tensile strength of each of said solid-state spheres and/or ellipsoids, e.g., in the range of from about 5,000 psi to about 12,000 psi, with the range of mass ratios of said plurality of spheres and/or ellipsoids:semi-solid substrate sections being in the range of from about 20:1 to about 100:1;

(iii) analyte collection means located downstream from said hollow enclosure means and communicating with said exit port means thereof, consisting essentially of tube trapping means whereby analyte mixture components emitted from said hollow enclosure means during gas flow therethrough and simultaneous operation of said horizontally-situated oscillatably-movable horizontal substantially solid substantially planar surface are entrapped in said tube trapping means; and (iv) upstream from said hollow enclosure means or downstream from said analyte collection means, gas flow-effecting means for effecting the flow of gas sequentially (I) from a location upstream from said first entry port means; (II) through said first entry port means; (III) into said hollow enclosure means in a direction substantially perpendicular to the plane of said base; (IV) past each of said plurality of spheres and/or ellipsoids; (V) through said exit port means of said hollow enclosure means and (VI) into and through said analyte collection means.

In addition, our invention is directed to a process for carrying out collection of analyte for the purpose of effecting quantitative and qualitative analysis of a volatile analyte composition encapsulated in a plurality of rupturable microcapsules each of which (a) has a rupturable polymeric wall; (b) has an outside diameter in the range of from about 0.01 microns to about 1000 microns and has a wall thickness in the range of from about 0.01 microns to about 100 microns; (c) contains from about 50% to about 97% by weight of volatile substance or solution of volatile substance; and (d) is releasably adhered to the surface of a semi-solid substrate section, comprising the steps of:

i. providing the apparatus of our invention as defined above;

ii. placing into the void space of said hollow enclosure means (I) layers of a plurality of mobile solid-state spheres and/or ellipsoids each of which has a weight of from about 1 gm to about 100 gm, a density of from about 2 gm/cc to about 10 gm/cc, an average diameter of from about 0.5 cm to about 3.0 cm, a tensile strength of from about 60,000 psi to about 300,000 psi, and a surface hardness Knoop value of from about 160 to about 220 or a Mohs hardness value in the range of from about 4 to about 8.5 or a Brinell hardness value in the range of from about 110 to about 750 and (II) inter-leaved between layers of said plurality of spheres and/or ellipsoids, semi-solid substrate sections having laminar surfaces, each of which has adhered thereto a plurality of said volatile substance-containing rupturable microcapsules each of which has a surface hardness Knoop value of from about 10 to about 20 or a Mohs hardness value in the range of from about 0.5 to about 2.0 or a Brinell hardness value in the range of from about 2 to about 15 and a microcapsule wall tensile strength several orders of magnitude less than the tensile strength of each of said solid-state spheres and/or ellipsoids, e.g., in the range of from about 5,000 psi to about 12,000 pounds per square inch (psi), with the range of mass ratios of said plurality of spheres and/or ellipsoids:semi-solid substrate sections being in the range of from about 20:1 to about 100:1;

iii. engaging said driving means for effecting a reciprocating motion of said substantially solid substantially planar surface;

iv. simultaneously with the engagement of said driving means for effecting an reciprocating motion of said substantially solid substantially planar surface, upstream from said hollow enclosure means, or downstream from said analyte collection means, effecting the flow of carrier gas sequentially (I) from a location upstream from said first entry port means; (II) through said first entry port means; (III) into said hollow enclosure means in a direction substantially perpendicular to the plane of said base; (IV) past each of said plurality of spheres and/or ellipsoids; (V) through said exit port means of said hollow enclosure means and (VI) into and through said analyte collection means whereby volatile substance components emitted from the microcapsules ruptured as a result of the spheres and/or ellipsoids abrading against them during operation of the apparatus are entrapped in said analyte collection means.

In practicing the process of our invention, the intensity of the functional product in the headspace above the abraded microcapsule is a function of (a) the time of operation, $\theta$, of said substantially solid substantially planar surface, (b) the frequency, $\phi$ or set of frequencies $\phi_1$, $\phi_2$, $\phi_3$, $\phi_n$ (wherein n is an integer in the range of from 1 to about 20) of the reciprocating motion of said substantially solid substantially planar surface, (c) the difference, $\Delta\tau$, between the average tensile strength of the polymeric microcapsule walls and the average tensile strength of the solid-state spheres and/or ellipsoids, (d)

the difference, $\Delta m$, between the average mass of each of the functional product-containing microcapsules and each of the solid-state spheres and/or ellipsoids and (e) the difference, $\Delta \chi$, between the average hardness of the polymeric microcapsule walls and the average hardness of the solid-state spheres and/or ellipsoids, in accordance with the mathematical relationship:

$$I = f(\phi, \theta, \Delta \tau, \Delta \chi, \Delta m)$$

Thus, the change of the intensity, $\Delta I$ (over a period of time, $\Delta \theta$) of the functional product in the headspace above the abraded microcapsule during the operation of the apparatus of our invention and when carrying out the process of our invention is in accordance with the mathematical relationship:

$$\Delta I = \int \left(\frac{\partial I}{\partial \theta}\right) d\theta + \int \left(\frac{\partial I}{\partial \phi}\right) d\phi + \int \left(\frac{\partial I}{\partial (\Delta \chi)}\right) d(\Delta \chi) + \int \left(\frac{\partial I}{\partial (\Delta \tau)}\right) d(\Delta \tau) + \int \left(\frac{\partial I}{\partial (\Delta m)}\right) d(\Delta m)$$

The intensity of the functional product in the headspace above the abraded microcapsule during the operation of the apparatus of our invention and when carrying out the process of our invention is in accordance with the algorithm:

$$I = 10 \Sigma M_i \int \cot(2\pi\phi\theta) d\theta = 10 \Sigma M_i [LN(\sin\{2\pi\phi\theta\})]$$

wherein $M_i$ is the mass of solid-state sphere and/or ellipsoid, $\phi$ is the number of reciprocations per minute for the reciprocating shaker and $\theta$ is the time elapsed from commencement of operation of the apparatus, in minutes.

The rate of functional product entering the trapping means is in accordance with the algorithm:

$$\frac{dM}{d\theta} = 20\pi\phi M[\cot(2\pi\phi\theta)]$$

and the amount of functional product collected in the trapping means as a function of time is in accordance with the algorithm:

$$LN M = 10 [LN \{\sin(2\pi\phi\theta)\}]$$

wherein M is the mass of functional product collected in the trapping means, $\phi$ is the number of reciprocations per minute for the reciprocating shaker and $\theta$ is the time elapsed from commencement of operation of the apparatus, in minutes.

The term, "reciprocating motion" is herein intended to include both (a) oscillating motion substantially in the horizontal plane, which includes the "X" and "Y" axes, but not the vertical "Z" axis, along a single axis, e.g., the "X" axis or the "Y" axis or on an axis intermediate therebetween, at an angle of 45° with reference to the "X' axis, or alternatively firstly along the "X' axis and secondly along the "Y' axis, or any combination of the foregoing and/or (b) rotary motion substantially in the horizontal plane.

DETAILED DESCRIPTION OF THE INVENTION

The Hollow Enclosure Means

Preferably the hollow enclosure means of the above-described apparatus is a cylindrical, or elliptical cylindrical, or frusto-conical enclosure impervious to gas except for an exit port, an entry port and an alternative entry port each of which is located in the lid or sidewall thereof. The material of construction and wall thickness of the hollow enclosure means are such that the enclosure structure is substantially rigid, and stable, being non-rupturable, to the internal impact of the mobile microcapsule-abrading solid objects, solid spheres and/or ellipsoids during apparatus operation. Thus, where the material of construction is glass, the preferred thickness thereof is in the range of from about 0.50 cm to about 3 cm and the hollow enclosure means preferably has a height dimension of from about 15 cm to about 50 cm and an effective diameter dimension or average diameter dimension of from about 10 cm to about 20 cm.

The Horizontally-Situated Reciprocating-Movable Solid Planar Surface

The hollow enclosure means of the above-described apparatus is held in place on the horizontally-situated reciprocating-movable solid planar surface by means of restrictive supports which cause the hollow enclosure means to remain in an upright configuration during the operation of the apparatus of our invention. Such restrictive supports are integral parts of the horizontally-situated reciprocating-movable solid planar surface on which the base of the hollow enclosure means is supported continuously during the operation of the apparatus of our invention. During operation of the apparatus of our invention, the movable solid planar surface may have a reciprocating oscillatory linear motion or a reciprocating rotary motion. Preferably, the movable solid planar surface is caused to have a reciprocating oscillatory linear motion at a frequency, $\phi$, in the range of from about 200 to about 300 reciprocations per minute; more preferably in the range of from about 260 to 290 reciprocations per minute. Such motion is effected as a result of the engagement of a specially-designed and constructed driving means which is associated with the movable solid planar surface. In carrying out the process of our invention, the driving means, and accordingly the movable solid planar surface supporting the hollow enclosure means is preferably operated for a period of time, $\theta$, in the range of from about 2 minutes to about 40 minutes, and more preferably in the range of from about 4 minutes to about 30 minutes. The prior art teaches a number of devices capable of being adapted for inclusion in the apparatus of our invention and in effecting the process of our invention, as set forth in the following Table 1:

TABLE I

| U.S. Patent or Published Patent Application | Title |
|---|---|
| U.S. Pat. No. 4,173,418 | Apparatus for mixing liquids |
| U.S. Pat. No. 5,971,599 | Reciprocating shaker apparatus |
| U.S. Pat. No. 6,579,002 | Broad-range large-load fast-oscillating high performance reciprocating programmable laboratory shaker |
| U.S. Patent Application 2001/0030906 | Electromagnetic vibratory microplate shaker |
| U.S. Patent Application 2003/0081499 A1 | Multidirectional shaker |

Preferably, the horizontally-situated reciprocatingly-movable solid planar surface useful in the practice of our invention is (a) the IKA (IKA-Werke GmbH & Co. KG of Staufen, Germany) Model KS 501 Digital Mixing Orbital Shaker with clamping roll attachment AS 501.1 or AS 501.2 or AS 501.3 or (b) the IKA Model HS 501 Digital Horizontal shaker with clamping roll attachment AS 501.1 or AS 501.2 or AS 501.3 or (b) the IKA Model HS 501 as described in the IKA blue line 2003 catalogue at pages 37 and 43. More preferable is the IKA Model HS 501 Digital Horizontal shaker with clamping roll attachment AS 501.1 or AS 501.2 or AS 501.3.

The Gas Flow-Effecting Means

After the functional product-containing microcapsule-bearing substrates, including a group of hair follicles, fabric sections or simulated skin sections, and microcapsule-abrading objects, such as solid-state spheres or ellipsoids, are introduced into the hollow enclosure means, and the hollow enclosure means is closed and is located on the horizontally-situated reciprocating-movable solid planar surface and held in place by means of restrictive supports, gas flow-effecting means is connected to the entry port when used with positive pressure application to effect gas flow, or to the exit end of the trapping means in the case of negative pressure or vacuum applied to effect gas flow. Thus, simultaneously with the engagement of the driving means for effecting reciprocating motion of the substantially solid substantially planar surface, carrier gas is forced through the hollow enclosure means past the microcapsule-bearing substrates and the mobile solid-state spheres and/or ellipsoids, and then out the hollow enclosure means through the exit port thereof into the trapping means which contains the trapping material. The carrier gas, such as nitrogen, air or carbon dioxide, is inert and non-reactive with the substrate, the microcapsule walls, the microcapsule contents, which become components of the headspace on rupture of the microcapsules, and the materials of which the solid-state spheres and/or ellipsoids are composed. The carrier gas can either be forced through the hollow enclosure means from a pressurized device upstream from the hollow enclosure means such as a pressurized carbon dioxide cylinder, or the carrier gas can be pulled through the hollow enclosure means using a vacuum pump located downstream from the trapping means, such as a vacuum pump. In the case of using a vacuum pump, it is preferable to use a vacuum pump of the low flow variety, for example Low Flow pumps marketed by the Ametek Company of Largo, Fla., called the Ametek Constant Flow Sampler. The flow rate of carrier gas past the microcapsule-bearing substrates and solid-state spheres and/or ellipsoids is preferably at a rate in the range of from about 20 ml per minute to about 200 ml per minute of carrier gas, such as nitrogen, air or carbon dioxide. Whether the inert gas flow-effecting means is upstream from the remainder of the apparatus or downstream from the remainder of the apparatus, it is preferable to have a gas filter in place in the apparatus of our invention, upstream from the hollow enclosure means so that the inert gas flowing past the microcapsule-bearing substrate and mobile solid-state spheres and/or ellipsoids and mixing with the headspace components exiting from the ruptured microcapsules is free of any contaminants which would interfere with the analysis of the functional product composition originally contained in the microcapsules adhered to the substrate.

The Trapping Means or Analyte Collection Means

With respect to the trapping means, also herein referred to as the analyte collection means, located downstream from the hollow enclosure means and communicating with the exit port means of the hollow enclosure means, the trapping means part of the apparatus of our invention comprises tube trapping means whereby volatile substance molecules emitted from the ruptured microcapsules during the simultaneous operation of (i) the horizontally-situated reciprocating-movable horizontal substantially solid substantially planar surface and (ii) gas flow past the microcapsule-bearing substrate and solid-phase spheres and/or ellipsoids, are entrapped in the tube trapping means. The tube trapping means preferably consists of a tube having a length in the range of from about 2 cm up to about 4 cm and a diameter of from about 0.1 cm up to about 0.4 cm. Thus, various trapping materials are useful in the practice of our invention. As stated above, TENAX is a preferable material. Various forms of TENAX are useful, for example, TENAX-GC. Other forms of TENAX and methods of production of such forms of TENAX are described in the U.S. Pat. Nos. 3,400,100; 3,644,227; 3,703,564; 4,431,779; and 4,801,645.

TENAX-GC is actually a polyphenyleneoxide defined according to the structure:

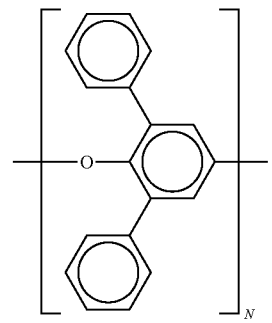

wherein N is an integer of from about 100 up to about 150.

Other trapping materials useful in the practice of our invention are as follows:

Activated Carbon marketed by Sigma-Aldrich Corporation of Milwaukee, Wis. 53201, U.S.A. (2003-2004 Catalog Nos. 16,155-1; 29,259-1; 24,223-3; 24,224-1; and 24,227-6 at page 39);

Activated Alumina marketed by Sigma-Aldrich Corporation of Milwaukee, Wis. 53201, U.S.A. (2003-2004 Catalog Nos. 19,996-6, 26,774-0, and 19,944-3 at page 62);

Silica Gels marketed by Sigma-Aldrich Corporation of Milwaukee, Wis. 53201, U.S.A (2003-2004 Catalog Nos. 60757; 21,439-6; and 21,441-8 at page 1646); and CHROMOSORB (Celite Corporation of Santa Barbara, Calif.), such as CHROMOSORB LC-1; CHROMOSORB LC-7; AND CHROMOSORB LC-9, marketed by Sigma Division of Sigma-Aldrich Corporation of St. Louis, Mo. 63178, U.S.A. (2002-2003 Catalog Nos. C 0641; C 6267; C 6142 and C 6269 at page 521).

The analytical apparatus means useful in the practice of our invention may contain, in place of the TENAX trapping substance, solid phase microextraction materials, known as SPME materials, such as those described in "Chomatography Products for Analysis and Purification", 2001 Catalog, published by SUPELCO Division of the Sigma-Aldrich Corporation., Supelco Park, Bellefonte, Pa. 16823-0048. A SPME example useful in the practice of our invention is 100 μm polydimethylsiloxane fiber, Catalog No. 57342-U of the Supelco Division of the Sigma-Aldrich Corporation. An additional description of the SPME technique useful in conjunction with the practice of our invention is the paper, Elmore, et al, *J. Agric. Food Chem.*, 1997, Volume 45, pages 2638-2641, entitled "Comparison of Dynamic Headspace Concentration on TENAX with Solid Phase Microextraction for the Analysis of Aroma Volatiles".

The Microcapsule

Descriptions of the microcapsule containing functional product, such as fragrance composition and/or malodour counteractant with which our invention is concerned is set forth in the following publications in Table II, below:

TABLE II

| Publication | Constituency of Microcapsule Wall |
|---|---|
| U.S. Pat. No. 2,800,458 | gelatin |
| U.S. Pat. No. 4,087,376 | urea-formaldehyde polymer |
| U.S. Pat. No. 4,100,103 | melamine-formaldehyde polymer |
| U.S. Pat. No. 4,157,983 | urea-formaldehyde polymer |
| U.S. Pat. No. 4,493,869 | urea-formaldehyde polymer |
| U.S. Pat. No. 6,248,364 | polyurethane |
| U.S. Patent Application 2003/0125222 A1 | acrylic acid and/or methacrylic acid polymer cross-linked with a melamine-formaldehyde pre-condensate |
| U.S. Patent Application 2003/0176282 | Various, including alkyl acrylate-acrylic acid copolymer, gelatin-gum arabic, melamine-formaldehyde polymer and methylated melamine-formaldehyde polymer |
| U.S. Patent Application 2003/0185960 A1 | Maillard reaction products of a protein and a carbohydrate |
| U.S. Patent Application 2003/0194416 A1 | Various, including methyl vinyl ether-maleic anhydride copolymer and polystyrene-acrylic acid copolymer |
| UK Patent Application GB 2,073,132 A | Various polymers, e.g. acrylamide/acrylic acid copolymer cross-linked with a melamine-formaldehyde pre-condensate |
| PCT Patent Application WO 98/28396 | Polyalkyl acrylates modified with a polyvinyl alcohol |
| De et al., "Brimonidine formulation in polyacrylic acid nanoparticles for ophthalmic delivery", J. Microencapsulation, 2003, Vol. 20, No. 3, pp 361-374 | Polyacrylic acid |

Preferably, the microcapsule wails of the microcapsules are composed of an aminoplast resin, more specifically a substituted or un-substituted acrylic acid polymer or co-polymer cross-linked with a urea-formaldehyde pre-condensate or a melamine-formaldehyde pre-condensate. The microcapsule is formed by means of either (a) forming an aqueous dispersion of a non-cured aminoplast resin by reacting under acidic pH conditions a urea-formaldehyde pre-condensate or a melamine-formaldehyde pre-condensate with one or more substituted or un-substituted acrylic acid polymers or co-polymers; then coacervating the resulting non-cured aminoplast resin shell about the surface of a fragrance and/or malodour counteractant-solvent monophasic droplet under homogenization conditions, such as using a homogenization apparatus as described in U.S. Pat. No. 6,042,792 and illustrated in FIGS. 11A and 11B thereof; and then curing the microcapsule shell wall at an elevated temperature, of from about 50-85° C. or (b) forming the aminoplast resin wall at the surface of the fragrance and/or malodour counteractant - solvent monophasic droplet by means of reacting, at the surface of the droplet a urea-formaldehyde pre-condensate or a melamine-formaldehyde pre-condensate with one or more substituted or un-substituted acrylic acid polymers or copolymers, and then curing the microcapsule shell wall at an elevated temperature, of from about 50-85° C.

Microcapsule formation using mechanisms similar to the foregoing mechanism, using (i) melamine-formaldehyde or urea-formaldehyde pre-condensates and (ii) polymers containing substituted vinyl monomeric units having proton-donating functional group moieties, such as, sulfonic acid groups or carboxylic acid anhydride groups, bonded thereto is disclosed in U.S. Pat. No. 4,406,816, describing 2-acrylamido-2-methyl-propane sulfonic acid groups, UK published Patent Application GB 2,062,570 A, describing styrene sulfonic acid groups; and UK published Patent Application GB 2,006,709 A, describing carboxylic acid anhydride groups.

The cross-linkable acrylic acid polymer or co-polymer microcapsule shell wall precursor has a plurality of carboxylic acid moieties,

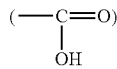

and is preferably one or a blend of the following:
(i) an acrylic acid polymer;
(ii) a methacrylic acid polymer;
(iii) an acrylic acid-methacrylic acid co-polymer;
(iv) an acrylamide-acrylic acid co-polymer;
(v) a methacrylamide-acrylic acid co-polymer;
(vi) an acrylamide-methacrylic acid co-polymer;
(vii) a methacrylamide-methacrylic acid co-polymer;
(viii) a $C_1$-$C_4$ alkyl acrylate-acrylic acid co-polymer;
(ix) a $C_1$-$C_4$ alkyl acrylate-methacrylic acid co-polymer;
(x) a $C_1$-$C_4$ alkyl methacrylate-acrylic acid co-polymer;
(xi) a $C_1$-$C_4$ alkyl methacrylate-methacrylic acid co-polymer;
(xii) a $C_1$-$C_4$ alkyl acrylate-acrylic acid-acrylamide co-polymer;
(xiii) a $C_1$-$C_4$ alkyl acrylate-methacrylic acid-acrylamide co-polymer;
(xiv) a $C_1$-$C_4$ alkyl methacrylate-acrylic acid-acrylamide co-polymer;
(xv) a $C_1$-$C_4$ alkyl methacrylate-methacrylic acid-acrylamide co-polymer;
(xvi) a $C_1$-$C_4$ alkyl acrylate-acrylic acid-methacrylamide co-polymer;
(xvii) a $C_1$-$C_4$ alkyl acrylate-methacrylic acid-methacrylamide co-polymer;
(xviii) a $C_1$-$C_4$ alkyl methacrylate-acrylic acid-methacrylamide co-polymer; and
(xix) a $C_1$-$C_4$ alkyl methacrylate-methacrylic acid-methacrylamide co-polymer.

and more preferably, an acrylic acid-acrylamide copolymer.

When substituted or un-substituted acrylic acid co-polymers are employed in the microcapsule structure, in the case of using a co-polymer having two different monomeric units, such as, acrylamide monomeric units and acrylic acid monomeric units, the mole ratio of the first monomeric unit to the second monomeric unit is in the range of from about 1:9 to about 9:1, preferably from about 3:7 to about 7:3. In the case of using a co-polymer having three different monomeric units, such as, ethyl methacrylate, acrylic acid and acrylamide, the mole ratio of the first monomeric unit to the second monomeric unit to the third monomeric unit is in the range of 1:1:8 to about 8:8:1, preferably from about 3:3:7 to about 7:7:3.

The molecular weight range of the substituted or un-substituted acrylic acid polymers or co-polymers employed in conjunction with our invention is from about 5,000 to about 1,000,000, preferably from about 10,000 to about 100,000.

The substituted or un-substituted acrylic acid polymers or co-polymers employed in conjunction with our invention may be branched, linear, star-shaped, dendritic-shaped or may be a block polymer or copolymer, or blends of any of the aforementioned polymers or copolymers. Substituted or un-substituted acrylic acid polymers or co-polymers may be prepared according to any processes known to those skilled in the art, for example, U.S. Pat. No. 6,545,084.

The urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. Our invention is particularly applicable where the resulting material has a molecular weight in the range of from 156 to 3000. The resulting material may be used 'as-is' as a cross-linking agent for the aforementioned substituted or un-substituted acrylic acid polymer or copolymer or it may be further reacted with a $C_1$-$C_6$ alkanol, such as, methanol, ethanol, 2-propanol, 3-propanol, 1-butanol, 1-pentanol or 1-hexanol, thereby forming a partial ether where the mole ratio of melamine or urea:formalhyde:alkanol is in the range of 1:(0.1-6):(0.1-6). The resulting ether moiety-containing product may by used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846; and 6,261,483, and Lee et al. J. Microencapsulation, 2002, Vol. 19, No. 5, pp 559-569, "Microencapsulation of fragrant oil via in situ polymerization: effects of pH and melamine-formaldehyde molar ratio". Examples of urea-formaldehyde pre-condensates useful in the practice of our invention are URAC 180 and URAC 186, Cytec Technology Corp., Wilmington, Del. 19801, U.S.A. Examples of melamine-formaldehyde pre-condensates useful in the practice of our invention are CYMEL U-60, CYMEL U-64 and CYMEL U-65, Cytec Technology Corp., Wilmington, Del. 19801, U.S.A. With reference to the microencapsulates employed in conjunction with our invention it is preferable to use as the precondensate for cross-linking the substituted or un-substituted acrylic acid polymer or co-polymer the melamine-formaldehyde pre-condensate having the structure:

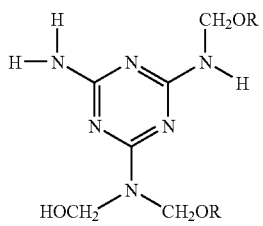

wherein each of the R groups are the same or different and each represents hydrogen or $C_1$-$C_6$ lower alkyl, e.g., methyl, ethyl, 1-propyl, 2-propyl, 1-butyl, 2-butyl, 2-methyl-1-propyl, 1-pentyl, 1-hexyl and/or 3-methyl-1-pentyl.

Furthermore, with reference to the microencapsulates employed in conjunction with our invention, the range of mole ratios of urea-formaldehyde precondensate or melamine-formaldehyde pre-condensate:substituted or un-substituted acrylic acid polymer or co-polymer is in the range of from about 9:1 to about 1:9, preferably from about 5:1 to about 1:5 and most preferably from about 1:2 to about 2:1.

The Substrate

As stated above, the microcapsule-bearing substrate employed in conjunction with our invention may be one or more fabric sections, one or more groups of hair follicles or one or more simulated skin sections. With reference to the substrates, it is preferable during and immediately subsequent to the operation of the apparatus of our invention, that the substrate section have such a structure and such dimensions that it remains intact in order to prevent particles thereof from being entrained in the gas stream entering the trapping means. Accordingly, it is preferable that each of the fabric or simulated skin substrate sections has an effective diameter, or average diameter in the range of from about 5 cm to about 40 cm, a thickness in the range of from about 0.01 cm to about 0.3 cm and a tensile strength greater than about 1000 psi. Simulated skin substrates useful in conjunction with the practice of our invention are set forth in U.S. Pat. No. 4,832,978 and U.S. Patent Publications 2002/0098761 and 2003/0069482 A1.

The Microcapsule-Abrading Objects

In practicing our invention, preferable microcapsule-abrading objects are spheres or ellipsoids composed of a material having a tensile strength in the range of from about 60,000 psi to about 300,000 psi and a surface hardness Brinell value in the range of from about 4 to about 8.5, more preferably, spheres composed of stainless steel. Still more preferably the stainless steel spheres are coated with a passivation coating in order to prevent functional product adsorption onto the solid-state sphere and/or ellipsoid during the operation of the apparatus of our invention. Such passivation coating is most preferably in the alternative, silicon having a thickness in the range of from about 120 angstroms to about 500 angstroms or a silica coating having a thickness in the range of from about 0.5 microns to about 2 microns, for example, a SILCOSTEEL (Restek Corporation of Bellefonte, Pa.,) coating which is a de-activated fused silica coating or a SULFINERT (Restek Corporation) coating. Stainless steel spheres thus coated with a passivation coating may be prepared according to a process as disclosed in one of the U.S. patents or U.S. patent applications, as set forth in the following Table III:

TABLE III

| U.S. Patent or Published Patent Application | Type of Coating |
|---|---|
| U.S. Pat. No. 6,444,326 | Silicon |
| U.S. Pat. No. 6,511,760 | Silicon |
| U.S. Patent Application 2002/0099121 | Silica |

The mass ratio of microcapsule-abrading objects, e.g. the solid-state spheres and/or ellipsoids:substrate is in the range of from about 20:1 to about 100:1. In the case of the microcapsule-bearing fabric substrate, the mass ratio is preferably in the range of from about 50:1 to about 60:1. In the case of the microcapsule-bearing hair follicle substrate, the mass ratio is in the range of from about 35:1 to about 40:1.

DETAILED DESCRIPTION OF THE DRAWINGS

Figure 1A:
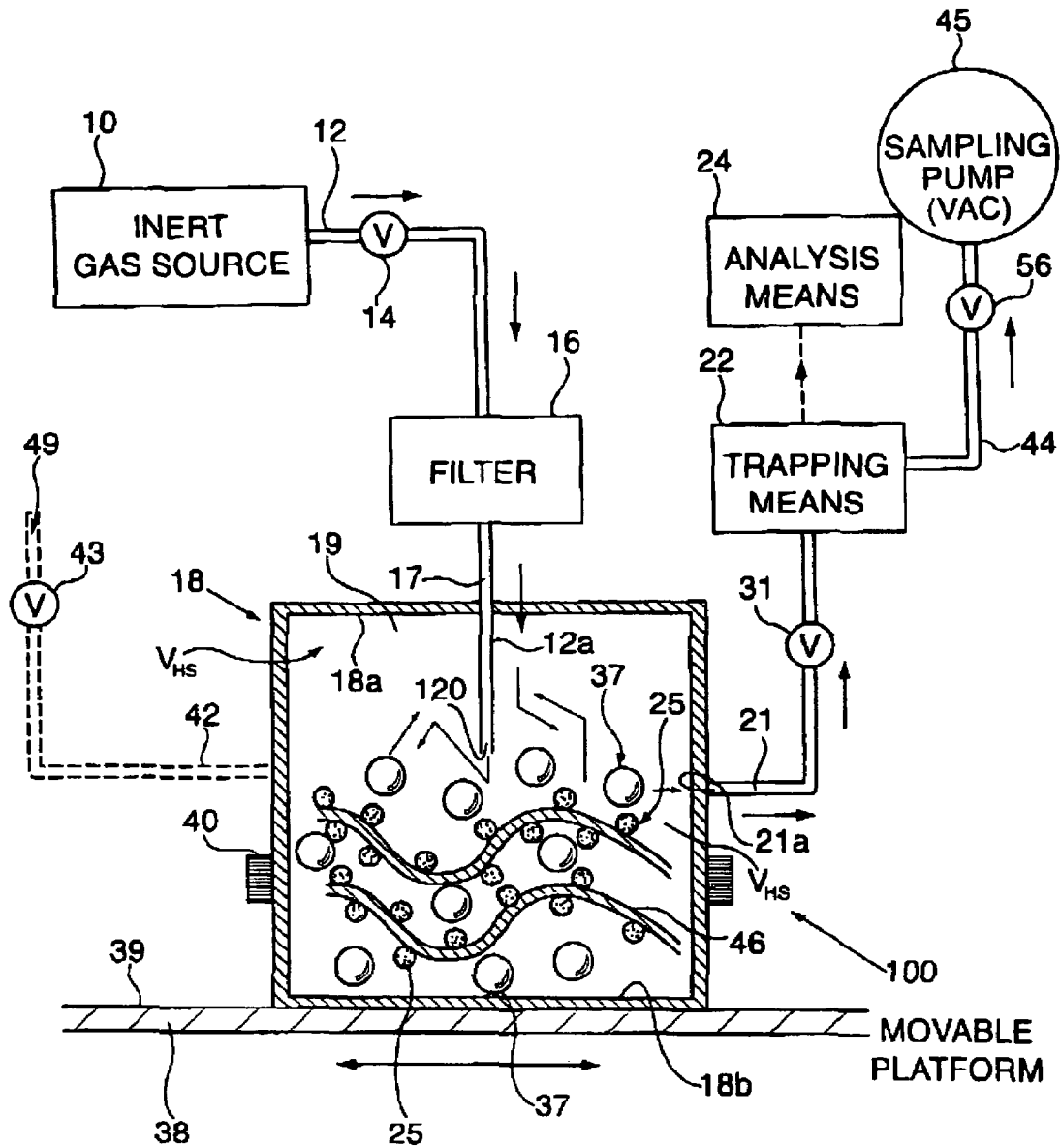
FIG. 1A is a schematic cut-away side elevation view of a first embodiment of the apparatus of our invention during operation thereof showing microcapsule-bearing fabric or hair or simulated skin substrates being abraded while simultaneously collecting headspace analyte in a trapping means during vacuum pump-induced passage of inert gas through the headspace.
Figure 1B:
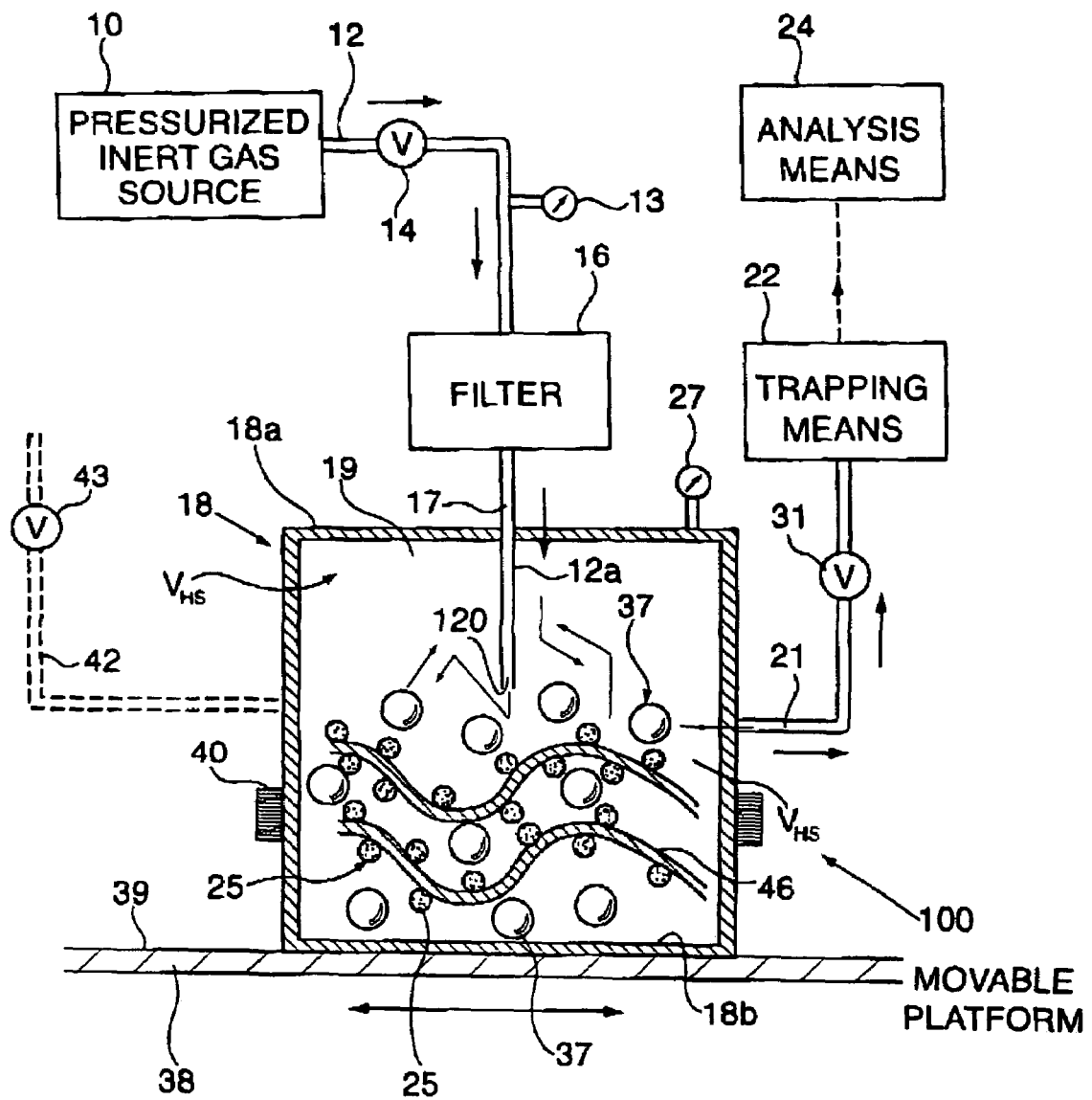
FIG. 1B is a schematic cut-away side elevation view of a second embodiment of the apparatus of our invention during operation thereof showing microcapsule-bearing fabric or hair or simulated skin substrates being abraded while simultaneously collecting headspace analyte in a trapping means during positive pressure pump-induced passage of inert gas through the headspace.
Figure 2:
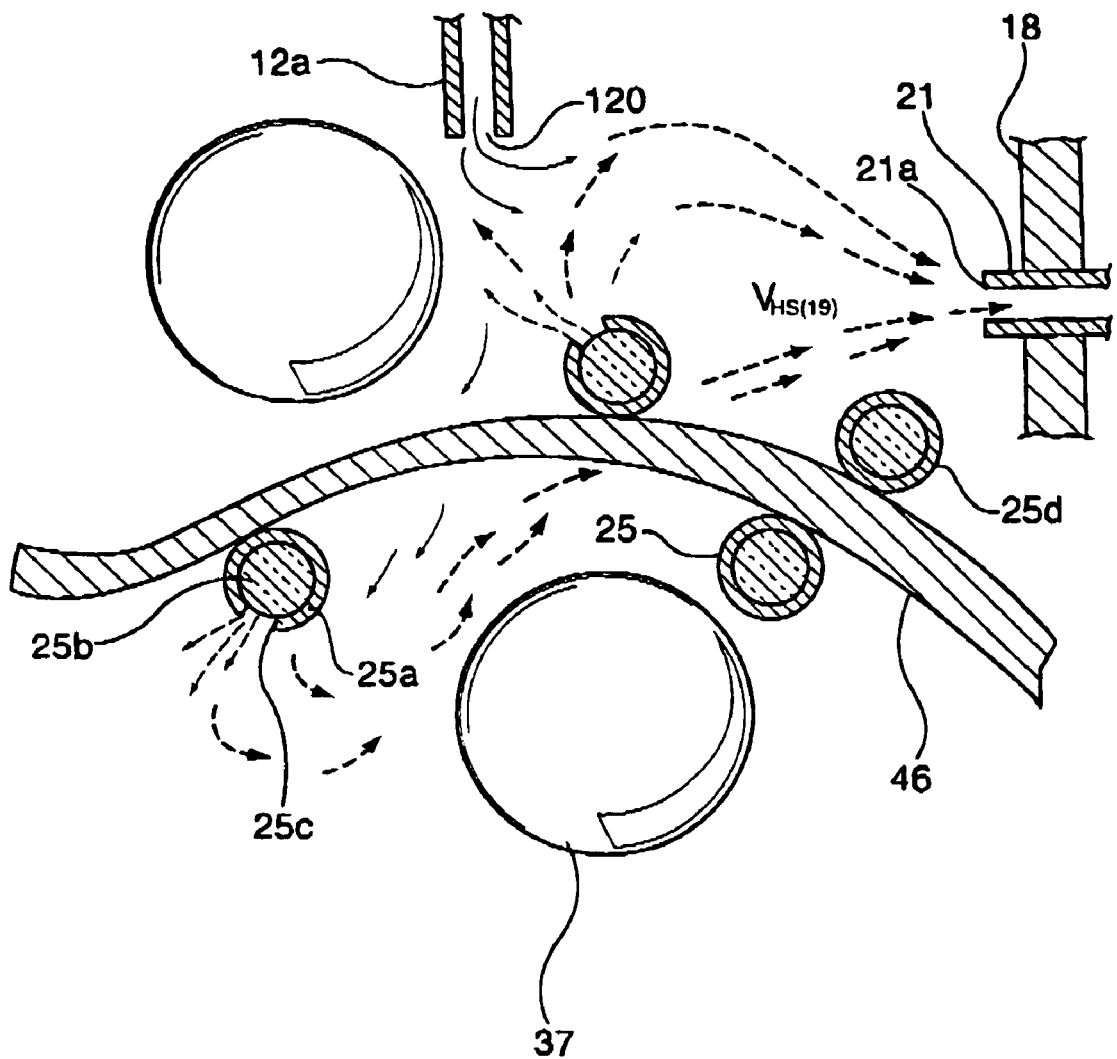
FIG. 2 is a schematic view of an enlargement of the illustration of FIG. 1A or FIG. 1B providing a detailed view of the operation of the apparatus in carrying out the process of our invention.
Figure 3:
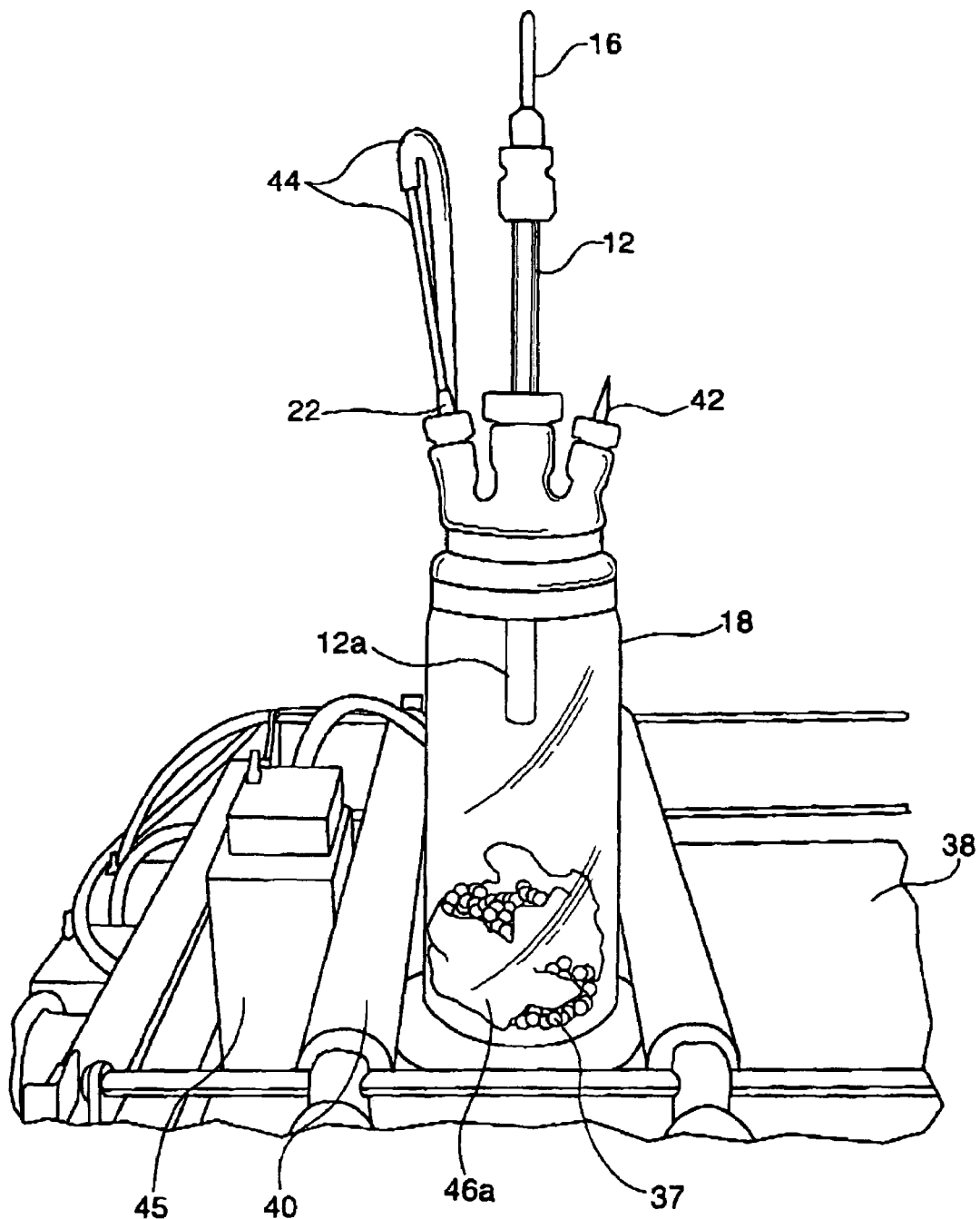
FIG. 3 is a perspective view of the apparatus of FIG. 1B immediately prior to carrying out the process of our invention, showing fragrance-containing microcapsule-bearing fabric ready to be abraded.
Figure 4:
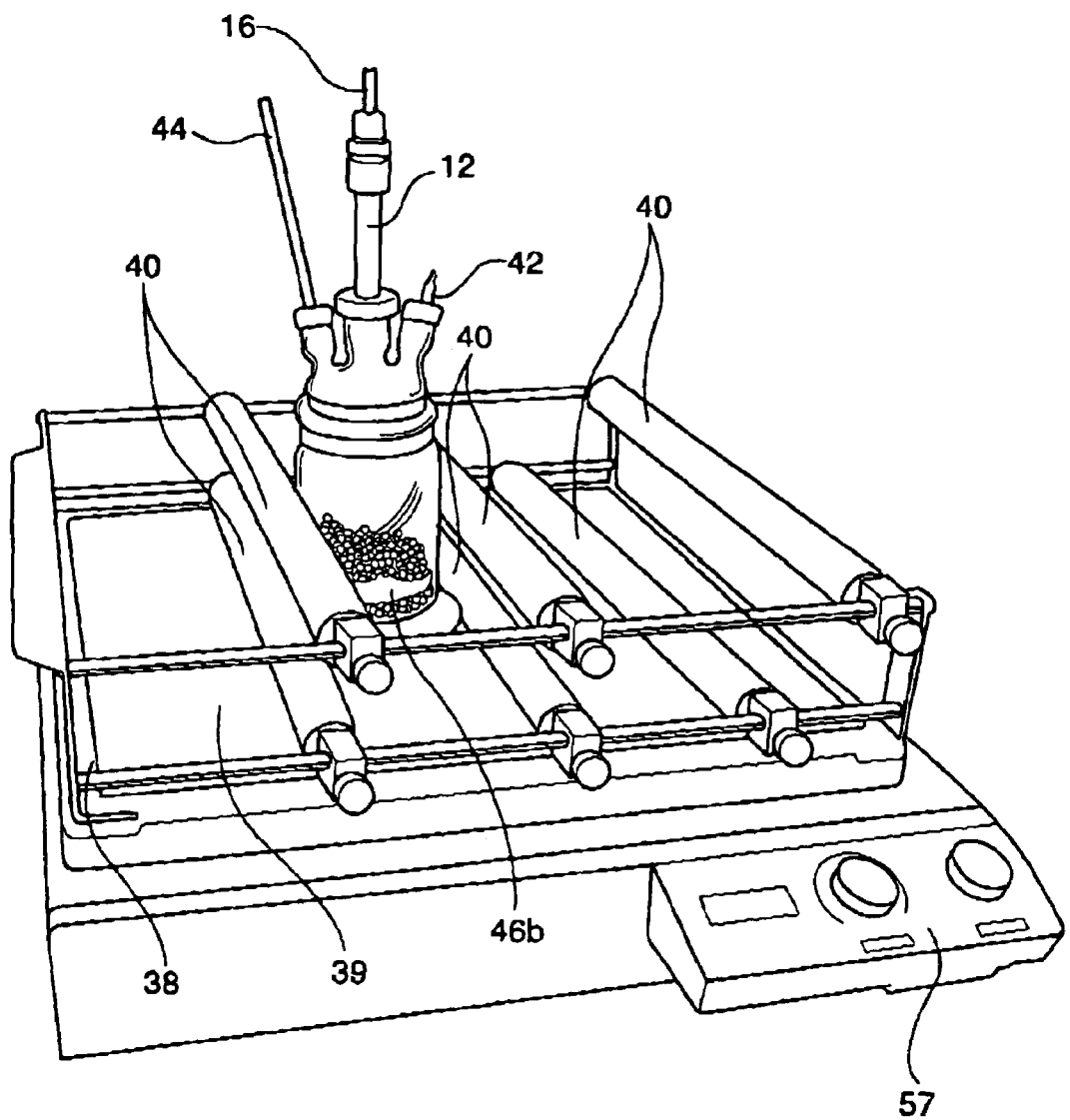
FIG. 4 is a perspective view of the apparatus of FIG. 1B immediately prior to carrying out the process of our invention, showing fragrance-containing microcapsule bearing groups of hair follicles ready to be abraded.

Referring to FIGS. 1A, 1B, 2, 3 and 4, fabric substrate sections, indicated by reference numeral 46a in FIG. 3, simulated skin substrate sections or hair follicle group substrates, indicated by reference numeral 46b in FIG. 4, all indicated by reference numeral 46 in FIGS. 1A, 1B and 2, having adhered thereto microcapsules 25 each containing functional product, such as, fragrance compositions and/or malodour counteractants is placed into the void space 19 of hollow enclosure means 18. Interleaved between the microcapsule-bearing substrates 46 are microcapsule-abrading solid objects which are stainless steel spheres 37 each being coated with a passivation coating. The base, 18b, of hollow enclosure means 18 is juxtaposed to the horizontally-situated reciprocanting-movable substantially solid substantially planar surface, 39 of a reciprocating movable platform, 38 associated with a driving means therefor 58 controlled using controls 57, shown in FIG. 4. The hollow enclosure means is held in place on the reciprocating movable platform 38 by the adjustable clamping rolls, 40. The driving means 58 is engaged, thereby causing the reciprocating-movable platform 38 to have an oscillatory movement at a frequency, $\phi$ in the range of from about 260 to 290 reciprocations per minute, thereby causing the solid-state stainless steel spheres 37 to become mobile within the hollow enclosure means, 18, and impinge upon the surfaces 25d of microcapsules 25, causing them to rupture whereby openings 25c are created in walls 25a of microcapsules 25 causing the functional product contents 25b to exit through openings 25c into headspace 19 (also shown as $V_{HS}$). Simultaneously with the engagement of driving means 58, gas, such as, air, nitrogen or carbon dioxide, from inert gas source 10 is passed through line 12 past valve 14 through carrier gas filter 16 through line 17-12a exiting from portal 120 into the void space $V_{HS}$ of hollow enclosure 18 where it mixes with the components of the functional products emitted from microcapsules 25. The mixture of functional product component and inert gas in headspace 19 then flows to exit portal 21a which is located at the entry of tube 21. The resulting gas-phase mixture is then passed through line 21 past valve 31 into and through trapping means 22 wherein components of the volatile functional product exiting from microcapsules 25 at openings 25c are trapped in a trapping material such as TENAX. The trapping substance containing the trapped components may then be extracted and the resulting extract analyzed in analysis means 24 including NMR, IR, GC and mass spectral analytical equipment. Overall the apparatus is indicated by reference numeral 100.

Specifically referring to FIGS. 1A and 3 during the operation of the apparatus of our invention, carrier gas from gas source 10 is pulled through the apparatus into the trapping means 22 and into the trapping substance located therein by means of vacuum pump means 45 located downstream from the trapping means 22. Inert carrier gas is pulled through the apparatus using vacuum pump means 45 through line 44 past control valve 56.

Optionally, when the trapping substance is saturated, and while it is being removed from the trapping means 22 for purposes of analysis, valve 31 is closed; operation of driving means 58 is temporarily discontinued; and operation of sampling vacuum pump 45 is temporarily discontinued. A second trapping means with sampling vacuum pump is then attached at location 49 to line 42 enabling additional sample to be collected in the second trapping means as the mixture of carrier gas and volatile functional product exiting from microcapsules 25 passes through line 42, past control valve 43 into the second trapping means.

Specifically referring to FIG. 1B, during the operation of the apparatus of our invention, pressurized gas, e.g., air, from for example a pressurized gas vessel 10 is passed through line 12 into the inner void space 19 of hollow enclosure means 18 through an entry port located in the lid 18a of hollow enclosure means 18. In FIG. 1B, pressure indicator 13 is located on line 12 and pressure indicator 27 is located in the lid 18a of hollow enclosure means 18 whereby a pressure drop from the entry of filter 16 to the exit port 21a is measured.

Optionally, when the trapping substance is saturated, and while it is being removed from the trapping means 22 for purposes of analysis, valve 31 is closed; operation of driving means 58 is temporarily discontinued; and operation of pressurized inert gas source 10 is temporarily discontinued. A second trapping means is then attached to line 42 enabling additional sample to be collected in the second trapping means as the mixture of carrier gas and volatile functional product exiting from microcapsules 25 passes through line 42, past control valve 43 into the second trapping means.

Figure 5:
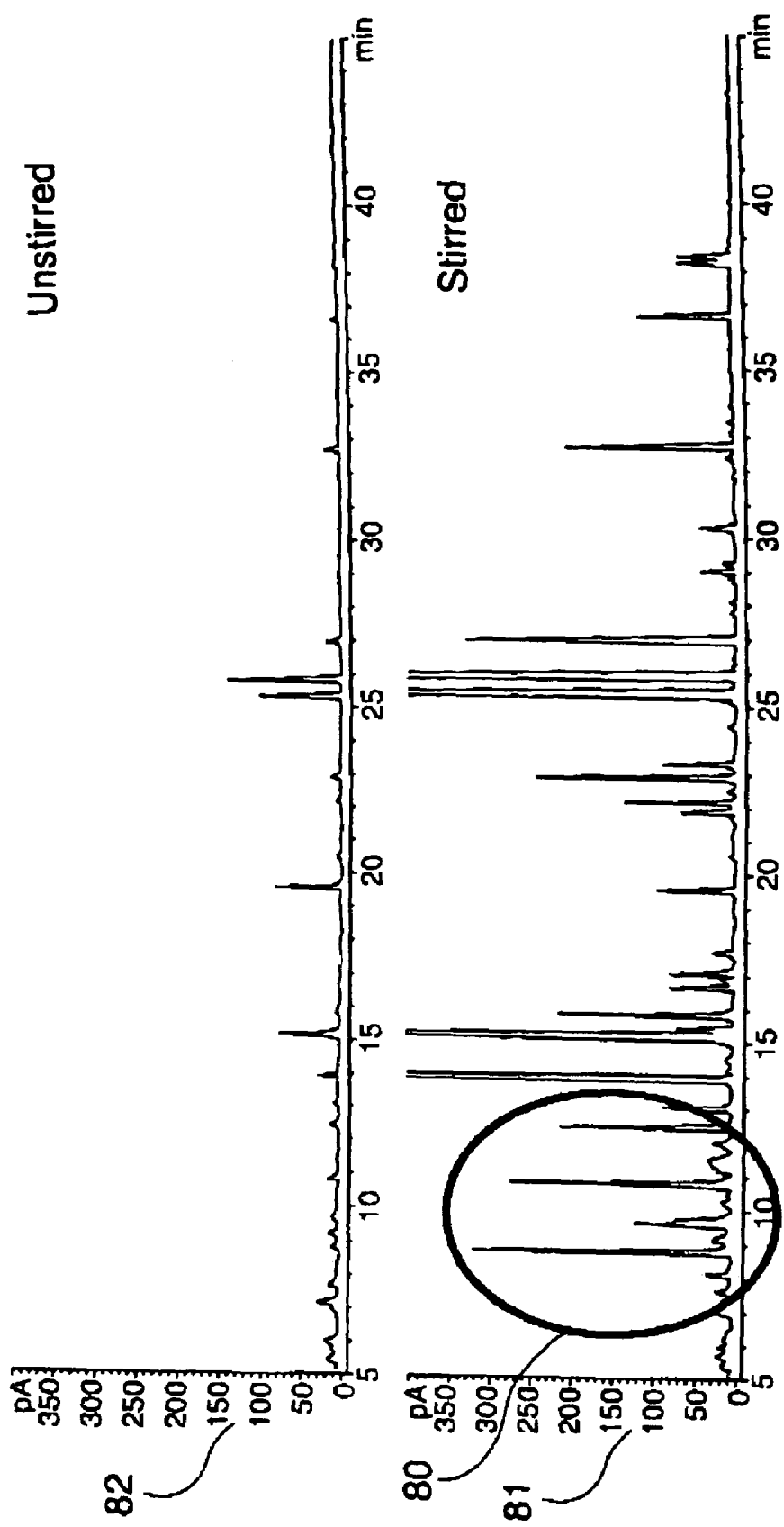
FIG. 5 sets forth two comparative gas capillary chromatograms of the GC headspace analysis of fragrance-containing microcapsule-bearing fabric samples: one (indicated by reference numeral 82) for fabric prior to operation of the apparatus of FIG. 3 and the second (indicated by reference numeral 81) during operation of the apparatus of FIG. 3.

The GC profile 82 of FIG. 5 indicates the gas chromatograph of headspace above fragrance-containing microcapsules produced according to Example B, infra, containing the fragrance of Example A, infra, prior to operation of the apparatus shown in FIG. 3. The microcapsules were adhered to two 4.5 inch×6 inch 100% cotton terrycloth swatches. The GC profile 81 of FIG. 5 indicates the gas chromatograph of headspace above ruptured microcapsules produced according to Example B, infra, containing the fragrance of Example A, infra, after carrying out the procedure of Example I, infra. The ruptured microcapsules were adhered to two 4.5 inch×6 inch 100% cotton terrycloth swatches. In each case, the chromatograph used was a Hewlett Packard 6890 GC and the GC conditions were as follows: A 50 meter×0.32 mm OV-1 column (Film thickness: 0.52 μm) programmed from 75° C. to 250° C. at 4° C./min, with a constant flow rate of 2.0 ml/min. The group of peaks indicated by reference numeral 80 in GC profile 81 is for the low molecular weight ingredients of the previously-encapsulated fragrance formulation. In each of the chromatographs, electrical response of the GC chromatograph is measured in picoamperes along the "Y" axis and time is measured in minutes along the "X" axis.

Figure 6:
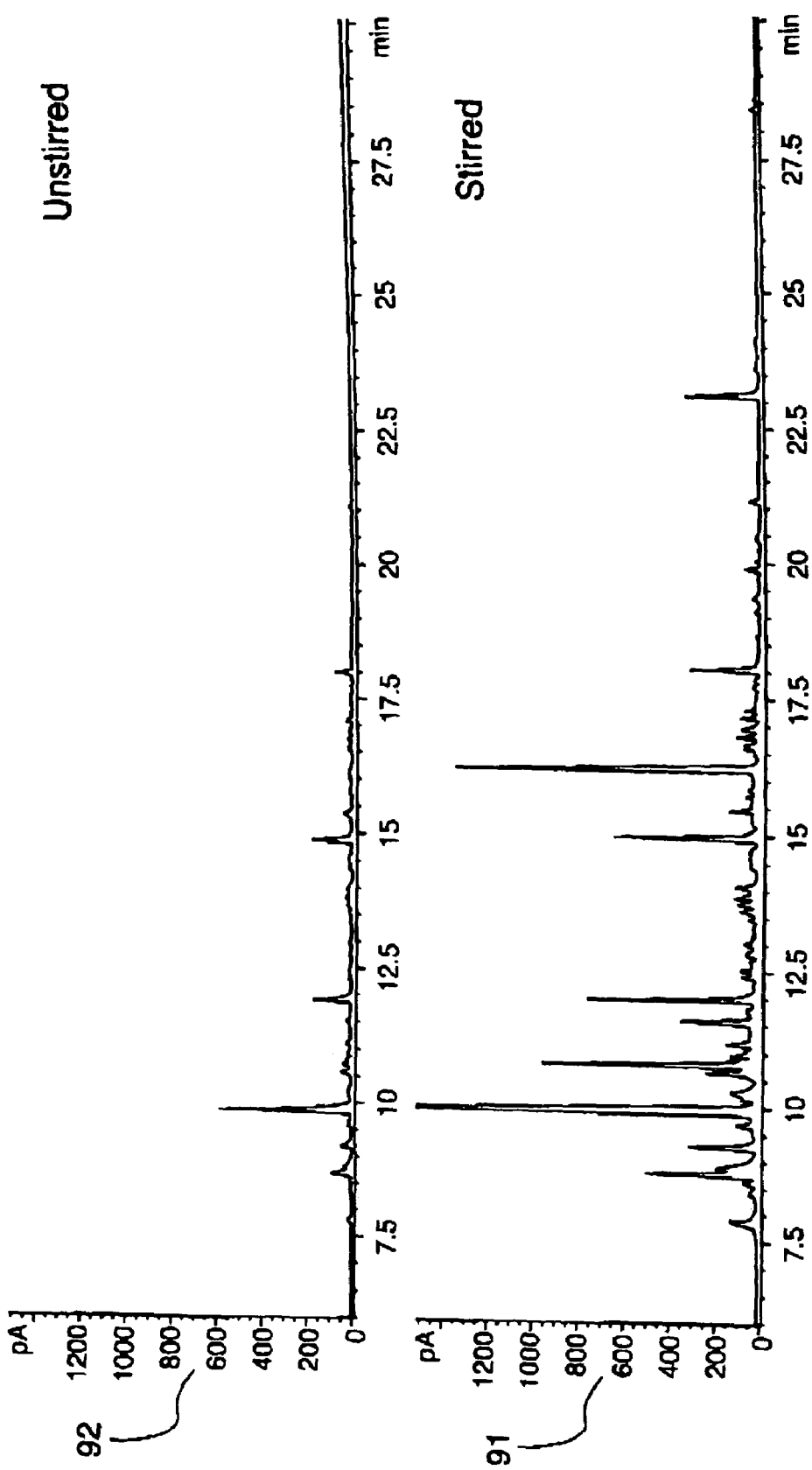
FIG. 6 sets forth two comparative gas capillary chromatograms of the GC headspace analysis of fragrance-containing microcapsule-bearing hair follicle group samples: one (indicated by reference numeral 92) for hair follicles prior to operation of the apparatus of FIG. 4 and the second (indicated by reference numeral 91) during operation of the apparatus of FIG. 4.

The GC profile 92 of FIG. 6 indicates the gas chromatograph of headspace above fragrance-containing microcapsules produced according to Example B, infra, containing the fragrance of Example A, infra, prior to operation of the apparatus shown in FIG. 4. The microcapsules were adhered to three 2.25 gram hair swatches trimmed to a total weight of 5.0 gm. The GC profile 91 of FIG. 6 indicates the gas chromatograph of headspace above ruptured microcapsules produced according to Example B, infra, containing the fragrance of Example A, infra, after carrying out the procedure of Example II, infra. The ruptured microcapsules were adhered to three 2.25 gram hair swatches trimmed to a total weight of 5.0 gm. In each case, the chromatograph used was a Hewlett Packard 6890 GC and the GC conditions were as follows: A 50 meter×0.32 mm OV-1 column (Film thickness, 0.52 μm) programmed from 75° C. to 250° C. at 4° C./min, with a constant flow rate of 2.0 ml/min. In each of the chromatograms, electrical response of the GC chromatograph is measured in picoamperes along the "Y" axis and time is measured in minutes along the "X" axis.

Figure 7A:
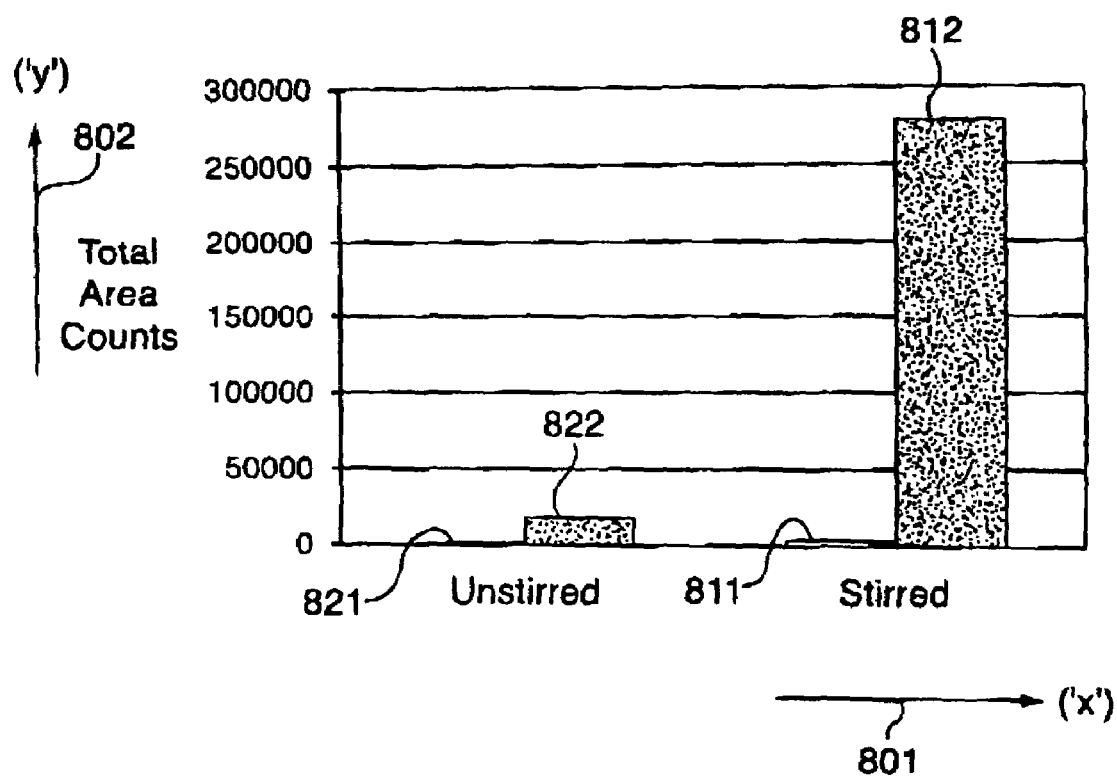
FIG. 7A is a set of bar graphs showing the comparison of the headspace above fabric substrate-bearing fragrance composition-containing microcapsules vs. the same fabric substrate containing unconfined fragrance (i) when the substrate is subjected to the process of our invention during operation of the apparatus of our invention, with mobile microcapsule-abrading objects, the stainless steel spheres, impinging upon and rupturing the microcapsules and (ii) when the substrate is in a quiescent state or unstirred, in the absence of mobile microcapsule-abrading objects impinging upon the microcapsules.
Figure 7B:
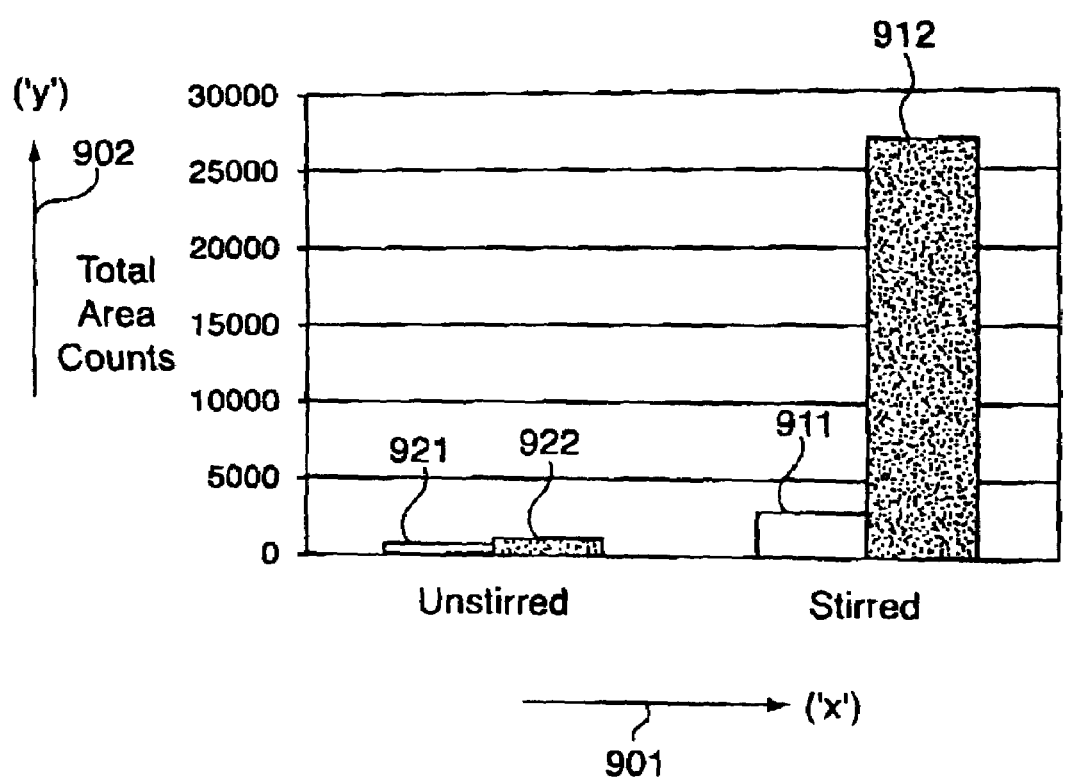
FIG. 7B is a set of bar graphs showing the comparison of the headspace above hair follicle group substrate-bearing fragrance composition-containing microcapsules vs. the same hair follicle group substrate-containing unconfined fragrance (i) when the hair follicle group substrate is subjected to the process of our invention during operation of the apparatus of our invention, with mobile microcapsule-abrading objects, the stainless steel spheres, impinging upon and rupturing the microcapsules and (ii) when the hair follicle group substrate is in a unstirred state, in the absence of mobile microcapsule-abrading objects impinging upon the microcapsules.

In FIGS. 7A and 7B, the measurement of total gas chromatogram area counts is along the "Y" axis which is indicated by reference numeral 802 in FIG. 7A and reference numeral 902 in FIG. 7B.

In FIG. 7A, the set of bar graphs showing the comparison of the headspace above fabric substrate-bearing fragrance composition-containing microcapsules vs, the same fabric substrate containing unconfined fragrance (i) when the substrate is subjected to the process of our invention during operation of the apparatus of our invention, with mobile microcapsule-abrading objects, stainless steel spheres, impinging upon and rupturing the microcapsules or non-confined fragrance-containing substrate, as the case may be and (ii) when the substrate is in a quiescent state (unstirred), in the absence of mobile microcapsule-abrading objects impinging upon the microcapsules or non-confined fragrance-containing substrate, as the case may be, is set forth along the "X" axis which is indicated by reference numeral 801. The bar graph indicated by reference numeral 821 is for fabric substrate containing unconfined fragrance when the substrate is in a unstirred state in the absence of mobile microcapsule-abrading objects impinging upon the unconfined fragrance-containing fabric. The bar graph indicated by reference numeral 822 is for fabric substrate-bearing fragrance composition-containing microcapsules when the substrate is in a unstirred state in the absence of mobile microcapsule-abrading objects impinging upon the microcapsules. The bar graph indicated by reference numeral 811 is for fabric substrate containing unconfined fragrance when the substrate is subjected to the process of our invention during operation of the apparatus of our invention, with mobile microcapsule-abrading objects, stainless steel spheres, impinging upon non-confined fragrance-containing substrate. The bar graph indicated by reference numeral 812 is for fabric substrate-bearing fragrance composition-containing microcapsules when the substrate is subjected to the process of our invention during operation of the apparatus of our invention, with mobile microcapsule-abrading objects, the stainless steel spheres, impinging upon and rupturing the microcapsules.

In FIG. 7B the set of bar graphs showing the comparison of the headspace above hair follicle group substrate-bearing fragrance composition-containing microcapsules vs. the same hair follicle group substrate containing unconfined fragrance (i) when the hair follicle group substrate is subjected to the process of our invention during operation of the apparatus of our invention, with mobile microcapsule-abrading objects, stainless steel spheres, impinging upon and rupturing the microcapsules or impinging upon the hair follicle group containing unconfined fragrance as the case may be and (ii) when the hair follicle group substrate is in an unstirred state, in the absence of mobile microcapsule-abrading objects impinging upon the microcapsule adhered to the hair follicle group or upon the hair follicle group containing the unconfined fragrance, as the case may be, is set forth along the "X" axis which is indicated by reference numeral 901. The bar graph indicated by reference numeral 921 is for the hair follicle group substrate containing unconfined fragrance when the substrate is in an unstirred state, in the absence of mobile microcapsule-abrading objects impinging upon the hair follicle group. The bar graph indicated by reference numeral 922 is for hair follicle group substrate-bearing fragrance composition-containing microcapsules when the substrate is in an unstirred state, in the absence of mobile microcapsule-abrading objects impinging upon the microcapsules. The bar graph indicated by reference numeral 911 is for hair follicle group substrate containing unconfined fragrance when the substrate is subjected to the process of our invention during operation of the apparatus of our invention, with mobile microcapsule-abrading objects, the stainless steel spheres, impinging upon non-confined fragrance-containing substrate. The bar graph indicated by reference numeral 912 is for hair follicle group substrate-bearing fragrance composition-containing microcapsules when the substrate is subjected to the process of our invention during operation of the apparatus of our invention, with mobile microcapsule-abrading objects, the stainless steel spheres impinging upon and rupturing the microcapsules.

The following examples are not meant to define or otherwise limit the scope of the invention. Rather the scope of the invention is to be ascertained according to the claims that follow the examples. Unless noted to the contrary, all percentages are given as a weight percent on a dry basis. As used throughout this specification and examples, cm is understood to mean centimeters, cc is understood to mean cubic centimeters and ml is understood to mean milliliters. Each of the specifications and claims of each of the U.S. Patents and U.S. Patent Applications cited herein are incorporated by reference as if set forth herein in their entirety.

EXAMPLE A

The following fragrance composition was prepared:

| Fragrance Component | Molecular Weight | Parts by Weight |
|---|---|---|
| ethyl undecylenate | 212.34 | 3.0 |
| geranyl anthranilate | 273.38 | 7.5 |
| α-irone | 206.33 | 6.3 |
| phenyl ethyl benzoate | 226.28 | 3.2 |
| d-limonene | 136.24 | 3.2 |
| cis-p-t-butylcyclohexyl acetat | 198.31 | 5.8 |
| amyl cinnamic aldehyde | 202.30 | 7.3 |
| hexyl cinnamic aldehyde | 216.33 | 12.6 |
| hexyl salicylate | 222.29 | 12.6 |

EXAMPLE B

50 Parts by weight of the fragrance of Example A was admixed with 50 parts by weight of NEOBEE-M5 (Stepan Chemical Company of Northfield, Ill., U.S.A.), the triglyceride ester of a mixture of caprylic acid and capric acid uses as a solvent thereby forming a fragrance/solvent composition. In a homogenizer as illustrated in FIGS. 11-A and 11-B of U.S. Pat. No. 6,042,792, fragrance/solvent composition-containing microcapsules were prepared by interfacial polymerization of a microcapsule wall encapsulating fragrance/solvent composition droplets. To make the capsule slurry, a copolymer of acrylamide and acrylic acid was first dispersed in water together with a methylated melamine-formaldehyde pre-condensate having the structure:

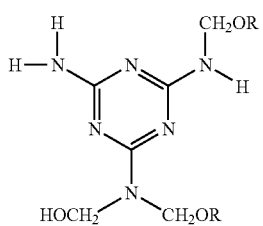

wherein one of the R moieties represents methyl and the other of the R moieties represents hydrogen. These two components were allowed to react under acidic conditions. The fragrance/solvent composition was then added into the solution and droplets of the desired size were achieved by high shear homogenization. Curing of the polymeric layer around the fragrance/solvent composition droplets was achieved by increasing the temperature to 50-85° C. The resulting capsule slurry contained 55% water, and 45% filled microcapsules, 35% core consisting of 50% fragrance of Example A, and 50% NEOBEE M-5 and 10% microcapsule wall.

EXAMPLE C

The slurry of microcapsules of Example B was formulated into the following suspended microcapsule slurry described in the table below:

| Ingredients | Parts by Weight |
|---|---|
| Slurry of Microcapsules of Example B | 0.30 |
| Water | 90.7 |
| SURCIDE P (hexahydro-1,3,5-tris(2-hydroxyethyl)-s-triazine available from Surety Laboratories of North Wales, Pennsylvania, U.S.A.) preservative | 0.10 |
| TOMADOL 91-8 (Tomah Products, Inc. of Milton, Wisconsin, U.S.A.)(Mixture of the hydroxy-octaethoxy ethers of n-nonanol and n-undecanol) ionic surfactant | 2.70 |
| Xanthan gum (suspension agent) | 0.50 |
| Dimethyl silicone polymer having the formula: $(CH_3)_3SiO[(CH_3)_2SiO]_6Si(CH_3)_2$ | 1.0 |

In addition, an unconfined fragrance formulation was prepared containing the following ingredients:

| Ingredients | Parts by Weight |
|---|---|
| Fragrance formulation of Example A | 0.05 |
| Water | 93.00 |
| SURCIDE P (hexahydro-1,3,5-tris(2-hydroxyethyl)-s-triazine available from Surety Laboratories of North Wales, Pennsylvania, U.S.A.) preservative | 0.10 |
| TOMADOL 91-8 (Tomah Products, Inc. of Milton, Wisconsin, U.S.A.)(Mixture of the hydroxy-octaethoxy ethers of n-nonanol and n-undecanol) ionic surfactant | 2.70 |

EXAMPLE I 150 cc of the suspended microcapsule slurry of Example C was placed in a first trigger sprayer as disclosed in U.S. Pat. No. 4,819,835. In addition, 150 cc of the unconfined fragrance formulation of Example C was placed in a second trigger sprayer as disclosed in U.S. Pat. No. 4,819,835.

Using the first trigger sprayer, 20 cc portions of the suspended microcapsule slurry were then sprayed onto each surface of two 4 inch×6 inch 100% cotton terrycloth swatches 46a, weight of 9 ounce per square yard with overcast stitch, produced by Testfabrics of West Pittston, Pa.

A first group of 200 g of 1 cm in diameter deactivated stainless steel ball bearings 37 coated with a silica coating of 1 micron thickness (Restek Corporation of Bellefonte, Pa., U.S.A., Part # 552130) was placed in void space 19 on base 18b of the hollow enclosure 18 (Volume: 1 liter; Custom glassware(Quark 800-955-0376)) of the apparatus of FIGS. 1A, 2 and 3. One of the resulting fabric swatches 46 having fragrance composition-containing microcapsules 25 adhered thereto the first fabric swatch, was then placed atop the first group of 200 g of deactrivated stainless steel ball bearings 37. A second group of 200 g of 1 cm in diameter deactivated stainless steel ball bearings 37 coated with a silica coating of 1 micron thickness was then placed on the surface of the first fabric swatch. A second fabric swatch was then placed atop the second group of 200 g of deactivated stainless steel ball bearings.

A lid was placed on the hollow enclosure 18 and a swage brass union with charcoal filter 16 was secured on the center tube 12-17. A TENAX trap 22 containing 150 mg of TENAX TA was attached to the tube/fitting 21 which leads to the exit port 21a of hollow enclosure 18. The TENAX trap was attached via tube 44 to sampling pump 45, a Gilian GilAir 3 portable automatic sampling pump with low flow option. The system was then allowed to equilibrate for 5 minutes. Over a period of 20 minutes, at a rate of 50 cc/minute, 1 liter of headspace was collected in the TENAX trap 22. This sample is identified as the unstirred sample, and the fragrance components are shown on the GC chromatogram indicated by reference numeral 82 of FIG. 5 and shown on the bar graph indicated by reference numeral 822 on FIG. 7A.

The TENAX trap 22 was then replaced with a clean TENAX trap 22 and the sampling pump, 45 was re-attached to tube 44. The system was allowed to equilibrate for 5 minutes while securing the hollow enclosure 18 on the surface, 39 of platform 38 of a flat bed shaker (IKA horizontal shaker, Model # HS 501 digital, manufactured by IKA-Werke GmbH & Co. KG, D 79219 Staufen, Germany) using the IKA universal attachment model #AS 501.1. The flat bed shaker driving means 58 was then engaged using controller 57, for operation at 275 reciprocations per minute for a period of 20 minutes during which 20 minute period, at a rate of 50 cc/minute, 1 liter of headspace was collected in the TENAX trap. The resulting sample is identified as the stirred sample and the fragrance components are shown on the GC chromatogram indicated by reference numeral 81 of FIG. 5 and shown on the bar graph indicated by reference numeral 812 of FIG. 7A.

Using the second trigger sprayer, 20 cc portions of the unconfined fragrance formulation was then sprayed onto each surface of two 4"×6" 100% cotton terrycloth swatches 46a.

A first group of 200 g of 1 cm in diameter deactivated stainless steel ball bearings 37 coated with a silica coating of 1 micron thickness was placed in void space 19 on base 18b of the hollow enclosure 18 of the apparatus of FIGS. 1A and 3. One of the resulting fabric swatches 46 having unconfined fragrance formulation adsorbed thereon, a first fabric swatch was then placed atop the first group of 200 g of deactrivated stainless steel ball bearings 37. A second group of 200 g of 1 cm in diameter deactivated stainless steel ball bearings 37 coated with a silica coating of 1 micron thickness was then placed on the surface of the first fabric swatch. A second fabric swatch was then placed atop the second group of 200 g of deactivated stainless steel ball bearings.

A lid was placed on the hollow enclosure 18 and a swage brass union with charcoal filter 16 was secured on the center tube 12-17. A TENAX trap 22 containing 150 mg of TENAX TA was attached to the tube/fitting 21 which leads to the exit port 21a of hollow enclosure 18. The TENAX trap was attached via tube 44 to sampling pump 45, A Gilian GilAir 3. The system was then allowed to equilibrate for 5 minutes. Over a period of 20 minutes, at a rate of 50 cc/minute, 1 liter of headspace was collected in the TENAX trap 22. This sample is identified as the unstirred sample, and the fragrance components are shown on the bar graph indicated by reference numeral 821 on FIG. 7A.

The TENAX trap 22 was then replaced with a clean TENAX trap 22 and the sampling pump, 45 was re-attached to tube 44. The system was allowed to equilibrate for 5 minutes while securing the hollow enclosure 18 on the surface, 39 of platform 38 of a flat bed shaker using the IKA universal attachment model #AS 501.1. The flat bed shaker driving means 58 was then engaged using controller 57, for operation at 275 reciprocations per minute for a period of 20 minutes during which 20 minute period, at a rate of 50 cc/minute, 1 liter of headspace was collected in the TENAX trap. The resulting sample is identified as the stirred sample and the fragrance components are shown on the bar graph indicated by reference numeral 811 of FIG. 7A.

EXAMPLE II 150 cc of the suspended microcapsule slurry of Example C was placed in a first trigger sprayer as disclosed in U.S. Pat. No. 4,819,835. In addition, 150 cc of the unconfined fragrance formulation of Example C was placed in a second trigger sprayer as disclosed in U.S. Pat. No. 4,819,835.

Using the first trigger sprayer, 20 cc portions of the suspended microcapsule slurry were then sprayed onto three 2.25 gram hair swatches and the swatches were then trimmed to a total weight of 5.0 grams ±0.1 g.

A first group of 137 g of 1 cm in diameter deactivated stainless steel ball bearings 37 coated with a silica coating of 1 micron thickness was placed in void space 19 on base 18b of the hollow enclosure 18 of the apparatus of FIGS. 1A, 2 and 4. The group of hair swatches 46 having fragrance composition-containing microcapsules 25 adhered thereto was then placed atop the first group of 137 g of deactivated stainless steel ball bearings 37. A second group of 137 g of 1 cm in diameter deactivated stainless steel ball bearings 37 coated with a silica coating of 1 micron thickness was then placed on the surface of the group of hair swatches.

A lid was placed on the hollow enclosure 18 and a swage brass union with charcoal filter 16 was secured on the center tube 12-17. A TENAX trap 22 containing 150 mg of TENAX TA was attached to the tube/fitting 21 which leads to the exit port 21a of hollow enclosure 18. The TENAX trap was attached via tube 44 to sampling pump 45. The system was then allowed to equilibrate for 5 minutes. Over a period of 4 minutes, at a rate of 50 cc/minute, 200 cc of headspace was collected in the TENAX trap 22. This sample is identified as the unstirred sample, and the fragrance components are shown on the GC chromatogram indicated by reference numeral 92 of FIG. 6 and shown on the bar graph indicated by reference numeral 922 on FIG. 7B.

The TENAX trap 22 was then replaced with a clean TENAX trap 22 and the sampling pump, 45 was re-attached to tube 44. The system was allowed to equilibrate for 5 minutes while securing the hollow enclosure 18 on the surface, 39 of platform 38 of a flat bed shaker using the IKA universal attachment model #AS 501.1. The flat bed shaker driving means 58 was then engaged using controller 57, for operation at 275 reciprocations per minute for a period of 5 minutes during which 5 minute period, at a rate of 50 cc/minute, 200 cc of headspace was collected in the TENAX trap. The resulting sample is identified as the stirred sample and the fragrance components are shown on the GC chromatogram indicated by reference numeral 91 of FIG. 6 and shown on the bar graph indicated by reference numeral 912 of FIG. 7B.

Using the second trigger sprayer, 20 cc portions of the unconfined fragrance formulation were then sprayed onto three 2.25 gram hair swatches and the swatches were then trimmed to a total weight of 5.0 grams±0.1 g.

A first group of 137 g of 1 cm in diameter deactivated stainless steel ball bearings 37 coated with a silica coating of 1 micron thickness was placed in void space 19 on base 18b of the hollow enclosure 18 of the apparatus of FIGS. 1A, 2 and 4. The trimmed hair swatch 46 having unconfined fragrance formulation adsorbed thereon was then placed atop the first group of 137 g of deactivated stainless steel ball bearings 37. A second group of 137g of 1 cm in diameter deactivated stainless steel ball bearings 37 coated with a silica coating of 1 micron thickness was then placed on the top surface of the trimmed hair swatch.

A lid was placed on the hollow enclosure 18 and a swage brass union with charcoal filter 16 was secured on the center tube 12-17. A TENAX trap 22 containing 150 mg of TENAX TA was attached to the tube/fitting 21 which leads to the exit port 21a of hollow enclosure 18. The TENAX trap was attached via tube 44 to sampling pump 45. The system was then allowed to equilibrate for 5 minutes. Over a period of 4 minutes, at a rate of 50 cc/minute, 200 cc of headspace was collected in the TENAX trap 22. This sample is identified as the unstirred sample, and the fragrance components are shown on the bar graph indicated by reference numeral 921 on FIG. 7B.

The TENAX trap 22 was then replaced with a clean TENAX trap 22 and the sampling pump, 45 was re-attached to tube 44. The system was allowed to equilibrate for minutes while securing the hollow enclosure 18 on the surface, 39 of platform 38 of a flat bed shaker (IKA horizontal shaker, Model # HS 501) using the IKA universal attachment model #AS 501.1. The flat bed shaker driving means 58 was then engaged using controller 57, for operation at 275 reciprocations per minute for a period of 5 minutes during which 5 minute period, at a rate of 50 cc/minute, 200 cc of headspace was collected in the TENAX trap. The resulting sample is identified as the stirred sample and the fragrance components are shown on the bar graph indicated by reference numeral 911 of FIG. 7B.

What is claimed is:

1. A process for carrying out a collection of analyte for the purpose of effecting quantitative and qualitative analysis of a volatile analyte composition encapsulated in a plurality of rupturable microcapsules each of which (a) has a rupturable polymeric wall; (b) has an outside diameter in the range of from about 0.01 microns to about 1000 microns and has a wall thickness in the range of from about 0.01 microns to about 100 microns; (c) contains from about 50% to about 97% by weight of volatile substance or solution of volatile substance; and (d) is releasably adhered to the surface of a semi-solid substrate section, comprising the steps of:
   (i) providing an apparatus;
   for quantitatively and qualitatively enabling the analysis of a volatile substance encapsulated in a plurality of rupturable microcapsules each of which (a) has a rupturable polymeric wall; (b) has an outside diameter in the range of from about 0.01 microns to about 1000 microns and has a wall thickness in the range of from about 0.01 microns to about 100 microns; (c) contains from about 50% to about 97% by weight of volatile substance or solution of volatile substance; and (d) is releasably adhered to the surface of a semi-solid substrate section, comprising:
   (a) a horizontally-situated reciprocatingly-movable horizontal substantially solid substantially planar surface located in the 'X-Y' plane associated with a driving means therefor for effecting a reciprocating motion of said substantially solid substantially planar surface at a controllable frequency $\phi$ or set of frequencies, $\phi_1, \phi_2, \phi_3, \phi_n$ (wherein n is an integer in the range of from 1 to about 20) for a determined period of time, $\theta$;
   (b) substantially removably supported on said substantially solid substantially planar surface, a hollow enclosure means having a void space surrounded by a gas-impermeable horizontally-disposed base, a gas-impermeable horizontally-disposed lid and a gas-impermeable substantially cylindrical wall extending upwardly from and circumventing said base and extending downwardly from and circumventing said lid, said lid and/or said cylindrical wall having at least one exit port means and an entry port means therethrough, said hollow enclosure means being maintained in a stable, rigid, upright configuration during operation of said apparatus and being adapted to stably contain (I) a plurality of mobile solid-state spheres and/or ellipsoids each of which has a weight of from about 1 gm to about 100 gm, a density of from about 2 gm/cc to about 10 gm/cc, an average diameter of from about 0.5 cm to about 3.0 cm and a surface hardness Knoop value in the range of from about 160 to about 220 and (II) inter-leaved between layers of said plurality of spheres and/or ellipsoids, semi-solid substrate sections having laminar surfaces, each of which has adhered thereto a plurality of said volatile substance-containing rupturable microcapsules each of which has a surface hardness Knoop value in the range of from about 10 to about 20 and a microcapsule wall tensile strength several orders of magnitude less than the tensile strength of each of said solid-state spheres and/or ellipsoids, with the range of mass ratios of said plurality of spheres and/or ellipsoids, semi-solid substrate sections being in the range of from about 20:1 to about 100:1;
   (c) analyte collection means located downstream from said hollow enclosure means and communicating with said exit port means thereof, consisting essentially of tube trapping means whereby analyte mixture components emitted from said hollow enclosure means during gas flow therethrough and simultaneous operation of said horizontally-situated oscillatably-movable horizontal substantially solid substantially planar surface are entrapped in said tube trapping means; and
   (d) upstream from said hollow enclosure means or downstream from said analyte collection means, gas flow-effecting means for effecting the flow of gas sequentially (I) from a location upstream from said first entry port means; (II) through said first entry port means; (III) into said hollow enclosure means in a direction substantially perpendicular to the plane of said base; (IV) past each of said plurality of spheres and/or ellipsoids; (V) through said exit port means of said hollow enclosure means and (VI) into and through said analyte collection means;
   (ii) placing into the void space of said hollow enclosure means (I) layers of a plurality of mobile solid-state spheres and/or ellipsoids each of which has a weight of from about 1 gm to about 100 gm, a density of from about 2 gm/cc to about 10 gm/cc, an average diameter of from about 0.5 cm to about 3.0 cm. and a surface hardness Knoop value of from about 160 to about 220 and (II) inter-leaved between layers of said plurality of spheres and/or ellipsoids, semi-solid substrate sections having laminar surfaces, each of which has adhered thereto a plurality of said and a microcapsule wall tensile strength several orders of magnitude less than the tensile strength of each of said solid-state spheres and/or ellipsoids, with the range of mass ratios of said plurality of spheres and/or ellipsoids; semi-solid substrate sections being in the range of from about 20:1 to about 100:1;
   (iii) engaging said driving means for effecting a reciprocating motion of said substantially solid substantially planar surface at a controllable frequency $\phi$ or set of frequencies, $\phi_1, \phi_2, \phi_3, \phi_n$ (wherein n is an integer in the range of from 1 to about 20) for a determined period of time, $\theta$;
   (iv) simultaneously with the engagement of said driving means for effecting an oscillating motion of said substantially solid substantially planar surface, upstream from said hollow enclosure means, or downstream from said analyte collection means, effecting the flow of carrier gas sequentially (I) from a location upstream from said first entry port means; (II) through said first entry port means; (III) into said hollow enclosure means in a direction substantially perpendicular to the plane of said base; (IV) past each of said plurality of spheres and/or ellipsoids; (V) through said exit port means of said hollow enclosure means and (VI) into and through said analyte collection means whereby volatile substance components emitted from the microcapsules ruptured as a result of the spheres and/or ellipsoids abrading against them during operation of the apparatus are entrapped in said analyte collection means whereby volatile substance components emitted from the microcapsules ruptured as a result of the spheres and/or ellipsoids abrading against them during operation of the apparatus are entrapped in said analyte collection means.

2. The process of claim 1 wherein the flow of carrier gas is effected upstream from said hollow enclosure means by means of pressurizing the carrier gas upstream from said hollow enclosure means.

3. The process of claim 1 wherein the flow of carrier gas is effected downstream from said analyte collection means using vacuum pump means located downstream from said analyte collection means.

4. The process of claim 3 wherein the said volatile substance is a fragrance; the walls of said microcapsules are composed of acrylic acid-acrylamide co-polymers cross-linked with a melamine-formaldehyde—methyl ether pre-condensate, and said spheres or ellipsoids are spheres fabricated from stainless steel.

5. The process of claim 4 wherein each of the rupturable microcapsules has an average diameter of from about 2.0 to about 15 microns and a wall thickness of from about 0.2 to 2.0 microns.

6. The process of claim 5 wherein the semi-solid section is selected from the group consisting of a fabric section, hair follicles and simulated human epidermis section.

7. The process of claim 6 wherein the microcapsules are coated with a cationic polymer.

8. The process of claim 4 wherein the mass ratio range of mass of stainless steel spheres:mass of hair follicles is from about 35:1 to about 40:1.

9. The process of claim 1 wherein said spheres or ellipsoids are spheres fabricated from stainless steel.

10. The process of claim 9 wherein the semi-solid section is selected from a group consisting of a fabric section, hair follicles and simulated human epidermis section.

11. The process of claim 10 wherein the mass ratio range of mass of stainless steel spheres:mass of fabric sections is from about 50:1 to 60:1.

12. The process of claim 9 wherein at least one of the steel balls is coated with a metal passivation coating which inhibits stainless steel ball surface adsorption of functional product.

13. The process of claim 12 wherein the metal passivation coating comprises a silica.

14. The process of claim 12 wherein the metal passivation coating is a silica coating having a thickness in the range of from about 0.5 microns to about 2.0 microns.

15. The process of claim 14 wherein the reciprocating motion of the substantially solid substantially planar surface is at a frequency, $\phi$, in the range of from about 260 to 290 reciprocations per minute, and the pre-determined period of time of operation of the apparatus, $\theta$, is in the range of from about 4 minutes to about 30 minutes.

16. The process of claim 12 wherein the metal passivation coating is a silicon coating having a thickness in the range of from about 120 to about 500 angstroms.

17. The process of claim 1 wherein the said volatile substance is a fragrance; the walls of said microcapsules are composed of acrylic acid-acrylamide co-polymers cross-linked with a melamine-formaldehyde—methyl ether pre-condensate, and said spheres or ellipsoids are spheres fabricated from stainless steel.

18. The process of claim 17 wherein each of the rupturable microcapsules has an average diameter of from about 2.0 to about 15 microns and a wall thickness of from about 0.2 to 2.0 microns.

19. The process of claim 1 wherein the intensity of the function product in the headspace as a function of time is in accordance with the algorithm:

$$I=10\Sigma M_i \int \cot(2\pi\phi\theta)d\theta = 10\Sigma M_i [LN(\sin\{2\pi\phi\theta\})]$$

wherein $M_i$ is the mass of an individual steel ball, $\phi$ is the number of reciprocations per minute for the reciprocating shaker and $\theta$ is the time elapsed from commencement of operation of the apparatus, in minutes.

20. The process of claim 19 wherein the microcapsules are coated with a cationic polymer.

21. The process of claim 1 wherein the rate of functional product entering the trapping means is in accordance with the algorithm:

$$\frac{dM}{d\theta} = 20\pi\phi M[\cot(2\pi\phi\theta)]$$

and the amount of functional product collected in the trapping means as a function of time is in accordance with the algorithm:

$$LN\,M=10[LN\{\sin(2\pi\phi\theta)\}]$$

wherein M is the mass of functional product collected in the trapping means, $\phi$ is the number of reciprocations per minute for the reciprocating shaker and $\theta$ is the time elapsed from commencement of operation of the apparatus, in minutes.

22. The process of claim 1 wherein the reciprocating motion of the substantially solid substantially planar surface is at a frequency, $\phi$, in the range of from about 200 to 300 reciprocations per minute, and the predetermined period of time of operation of the apparatus, $\theta$, is in the range of from about 2 minutes to about 40 minutes.

* * * * *